(12) United States Patent
Yip et al.

(10) Patent No.: US 10,624,579 B2
(45) Date of Patent: Apr. 21, 2020

(54) BIOFEEDBACK SYSTEM WITH BODY MAPPING CLOTHING FOR PATIENTS WITH ADOLESCENT IDIOPATHIC SCOLIOSIS

(71) Applicant: THE HONG KONG POLYTECHNIC UNIVERSITY, Hong Kong (HK)

(72) Inventors: Yiu-Wan Yip, Hong Kong (CN); Garcia Hin-Chun Kwok, Hong Kong (CN); Mei-Chun Cheung, Hong Kong (CN); Kit-Lun Yick, Hong Kong (HK)

(73) Assignee: THE HONG KONG POLYTECHNIC UNIVERSITY, Hong Kong (CN)

(*) Notice: Subject to any disclaimer, the term of this patent is extended or adjusted under 35 U.S.C. 154(b) by 257 days.

(21) Appl. No.: 15/947,897

(22) Filed: Apr. 9, 2018

(65) Prior Publication Data
US 2019/0307394 A1    Oct. 10, 2019

(51) Int. Cl.
*A61B 5/00* (2006.01)
*A61B 5/11* (2006.01)
(Continued)

(52) U.S. Cl.
CPC ............ *A61B 5/486* (2013.01); *A61B 5/0004* (2013.01); *A61B 5/0022* (2013.01);
(Continued)

(58) Field of Classification Search
CPC ..... A61B 5/486; A61B 5/1116; A61B 5/0024; A61B 5/742; A61B 5/0022; A61B 5/01;
(Continued)

(56) References Cited

U.S. PATENT DOCUMENTS

2016/0220174 A1* 8/2016 Yip .................. A61B 5/4561

OTHER PUBLICATIONS

Dolan L.A. et al., "Professional opinion concerning the effectiveness of bracing relative to observation in adolescent diopathic scoliosis", Journal of Pediatric Orthopaedics, 27(3): 270276, 2007.
(Continued)

*Primary Examiner* — Mark Bockelman
(74) *Attorney, Agent, or Firm* — Spruson & Ferguson (Hong Kong) Limited

(57) ABSTRACT

A biofeedback system for monitoring patient-related signals of a patient having adolescent idiopathic scoliosis (AIS) is disclosed. The present invention provides a personalized biofeedback to the patient based on the patient-related signals for restoring balance in muscle activities and reducing displacement of both sides of the patient's spine as a treatment for AIS. The biofeedback system comprises clothing integrated with posture monitoring sensors, and one or more computational systems comprising a sensor-based sEMG posture training subsystem for providing posture training and a posture monitoring subsystem for providing progressive training through daily activities. The sensor-based sEMG posture training subsystem comprises a posture training device coupled to a plurality of sEMG sensors, a feedback device and a calibration system. The posture monitoring subsystem monitors the posture of the patient and determines the properness of the posture by comparing the real-time data with the calibrated signals from the sEMG posture training subsystem.

19 Claims, 12 Drawing Sheets

(51) Int. Cl.
*A61B 5/0492* (2006.01)
*A61B 5/04* (2006.01)
*A61B 5/01* (2006.01)

(52) U.S. Cl.
CPC .............. *A61B 5/0024* (2013.01); *A61B 5/01* (2013.01); *A61B 5/04017* (2013.01); *A61B 5/0492* (2013.01); *A61B 5/1116* (2013.01); *A61B 5/4566* (2013.01); *A61B 5/6804* (2013.01); *A61B 5/742* (2013.01); *A61B 2503/06* (2013.01); *A61B 2505/09* (2013.01); *A61B 2560/0223* (2013.01); *A61B 2562/0219* (2013.01); *A61B 2562/043* (2013.01); *A61B 2562/063* (2013.01)

(58) Field of Classification Search
CPC . A61B 5/0004; A61B 5/04017; A61B 5/0492; A61B 5/6804; A61B 5/4566; A61B 2562/043; A61B 2503/06; A61B 2505/09; A61B 2560/0223; A61B 2562/0219; A61B 2562/063
See application file for complete search history.

(56) References Cited

OTHER PUBLICATIONS

Wong M.S., et al., "The Effect of Rigid Versus Flexible Spinal Orthosis on the Clinical Efficacy and Acceptance of the Patients With Adolescent Idiopathic Scoliosis", Spine, 33 (12), 1360-1365, 2008.
Dworkin, B., et al., "Behavioral Method for the Treatment of Idiopathic Scoliosis", Medical Sciences, 82 (8), 2493-2497, 1985.
Wong W., "Development of a posture monitoring system", Department of Health Technology and Informatics, The Hong Kong Polytechnic University, 2009.
Zeng Y.P., "3D Ultrasound Imaging for Assessment of Scoliosis", The Spine Journal, 12 (9), S164, 2012.
Zhu, Z., et al., "Genome-wide association study identifies novel susceptible loci and highlights Wnt/beta-catenin pathway in the development of adolescent idiopathic scoliosis", Human molecular genetics, 26, (8), 1577-1583, 2017.
Kwok, G., et al., "Postural Screening for Adolescent Idiopathic Scoliosis with Infrared Thermography", Scientific Report, Nature, 7:14431, Oct. 31, 2017.

\* cited by examiner a) Suggested standing position   b) Suggested sitting position

| Before Training | After Training |

| Before Training | After Training |

BIOFEEDBACK SYSTEM WITH BODY MAPPING CLOTHING FOR PATIENTS WITH ADOLESCENT IDIOPATHIC SCOLIOSIS

FIELD OF THE INVENTION

The present invention relates to a biofeedback system for monitoring patient-related signals of a patient having adolescent idiopathic scoliosis (AIS) and thereby enabling the patient to obtain a dynamic, personalized biofeedback based on the patient-related signals. In particular, the present invention relates to a biofeedback generated from computational systems based on surface electromyographic (sEMG) signals for providing progressive and tailored posture training to patient with AIS.

BACKGROUND

Adolescent idiopathic scoliosis (AIS) is a multi-factorial, three-dimensional deformity of the spine and trunk which can appear and sometimes progress during any of the rapid periods of growth in apparently healthy children. Generally, AIS patients are first diagnosed between the ages of 10 to 15 years old with skeletal maturity. Patients with early scoliosis or a Cobb's angle of 10-20 degrees only need to attend regular check-ups every 6 to 12 months. However, those patients with a spinal curvature of 21-45 degrees may undergo various kinds of therapy, whereas when the spinal curvature is over 45°, surgery is recommended by filling the vertebrae with bone through fusion to the spinal disc and thus straightening the spine [2]. For non-surgical and non-medical interventions for patients with a spinal curvature of 21-45 degrees, conventional orthotic interventions apply passive forces to the human body with orthosis with the use of a brace made of rigid plastic material to support the trunk alignment and control the deformities of the spine [4]. However, the use of these external supports is limited by factors such as poor appearance, bulkiness, physical constraint, skin irritation, and muscle atrophy that could lead to low acceptance and compliance. There are no differences even if a flexible brace, which is made of elastic bands, is used instead of a rigid brace [3]. Back muscle strengthening exercises attempt to strengthen the back muscles to maintain the trunk in an upright position with active muscular forces. However, patient compliance with the prescribed intervention exercises present a challenge, especially patients who are not self-motivated may not continue with the prescribed exercise programs.

There are a few existing works focusing on adopting sensor-based technology in treating idiopathic scoliosis. In WO2013110835A1, a programmable subcutaneous or submuscular device is proposed to collect/record electromyographic signals and stimulate that part of the deep paraspinal muscles that is affected by the pathology. The muscle stimulation is controlled by control logic that comprises a feedback-loop algorithm for adjustment of the stimulation on the basis of the results obtained from the sensors. There are many drawbacks regarding to this design. First, it is intrusive. The submuscular module requires proper procedure to be implanted into human body. This requirement largely affects comfort and compliance of the system, and even causes side effects such as infection. Second, it relies on a naive feedback loop. The feedback loop is implemented locally using predefined control logic. This imposes difficulty in modifying the feedback algorithm once the device is setup. More importantly, it has intrinsic inability to support adaptation of the feedback logic based either on the historical information such as patient's progress, or on external information such as doctor/specialists' opinion. Third, wired connection is adopted on the body area. Compared to wireless setup, wired design is less flexible, and less comfortable for the patient. Fourth, only electromyography is considered. It lacks the consideration of other important factors like patient's motion, posture, etc.

In U.S. Pat. No. 5,082,002A, a system and method for the operant conditioning of subjects using biofeedback is proposed. The design provides means to measure a variable condition, such as posture, which is controllable by the subject. The apparatus sets criteria, which, if not met, may result in a negative reinforcement, such as unpleasant audio tone or, if the criteria are met, will reward the subject. The criterion is automatically adjusted, upwards or downwards, in accordance with the subject's history of reaching, or not reaching, the criteria. Even though this design considered the aspect of adaptation, the adaptation method it used is very primitive—it is achieved by adjusting criteria upwards or downwards. In applications, however, the criteria are hard to set because multiple metrics (resulting to multitude of criteria) should be considered, let alone each criterion should vary from patient to patient. Hence, simply using criterion-based detection in this scenario is not sufficient. Another drawback of this design is that it proposed a tension-based sensor to detect the posture of the patients. Compared to a modern motion sensor, which utilizes accelerometer and gyroscope, the tension-based sensor lacks precision, flexibility, and is prone to error (due to the strict placement requirement).

In U.S. Pat. No. 6,984,208B2, a method for indirectly assessing the gesture, posture or movement of a body part of a person includes transmitting an ultrasound signal into the soft tissue of body part and manipulating the reflected ultrasound signal to obtain parameter data is provided. The method comprises applying an ultrasound transmitter and receiver to a musculoskeletal body part; transmitting an ultrasound signal into soft tissue of the body part and receiving a reflected and/or scattered ultrasound signal at the receiver; manipulating the ultrasound signal to obtain parameter data, including the amplitude, phase, flight-time, frequency spectrum and waveform pattern of the signal, and comparing the parameter data to reference information to obtain a gesture, posture, or movement of the body part. However, the effectiveness of the system for posture correction depends on its ability to remind the patient about his/her spinal curvature, either by alerting the patient of poor posture or by motivating him/her to straighten his/her spine. On this aspect, this proposed system is not preferable for a lack of effective means to stimulate and facilitate the patient in achieving an improvement in the posture in a progressive manner as a treatment for AIS.

Regarding the posture control, which is a major consideration for AIS treatment, the state-of-the art posture correction techniques usually consist of three abstract components: (1) feedback loop; (2) posture sensors; and (3) feedback means. Existing works on posture control are summarized in accordance with each respective component as follows.

Most of the designs, e.g., in WO2013110835A1, US20130108995A1, U.S. Pat. No. 8,157,752B2, U.S. Pat. No. 7,850,574B2, US20090054814A1, WO2006062423A1, U.S. Pat. No. 6,673,027B2 and U.S. Pat. No. 6,579,248B1, adopted a feedback loop with predefined (normally hard-coded) control logic, which we name as a naive feedback loop. The control logic or switch circuit is normally established based on one or a few preset criteria. The feedback means (such as an audio alert) is triggered when given criterion are reached. The whole control flow is normally implemented in hardware (using a switch circuit) as in U.S. Pat. Nos. 5,158,089A, 5,082,002A, 4,914,423A, 4,750,480A, 4,730,625A, 4,007,733A and 5,168,264A, or is hard-coded in software control logic on microcontrollers as in US20130108995A1, WO2013110835A1 and U.S. Pat. No. 8,157,752B2. As mentioned before, the naive feedback mechanism imposes difficulty in modifying the feedback algorithm once the device is set-up. More importantly, it has intrinsic inability to support adaptable feedback logic. Even with a training process implemented for updating the reference signals, as in U.S. Pat. No. 6,984,208B2, the reference information is still based on some typical postures when training the apparatus, which is similar to the abovementioned naive feedback mechanism with difficulties in correcting the data or adapting to changes after completing the training.

As for posture sensors, inclination (also pendulum) (U.S. Pat. Nos. 5,168,264A, 5,158,089A, US20090054814A1), tension (U.S. Pat. Nos. 4,007,733A, 4,914,423A, 5,082,002A, 5,728,027A, 6,384,729B1, 6,579,248B1, WO2006062423A1, US20080319364A1 and U.S. Pat. No. 8,083,693B1), flowable substance (U.S. Pat. No. 7,980,141B2), hinge (U.S. Pat. No. 6,673,027B2), distance between body and sensor (U.S. Pat. No. 8,157,752B2), have been used as sensory means for posture detection in earlier designs. While effectiveness of these methods is largely dependent on the application area and the positioning of sensory devices, the accuracy of a reading cannot always be maintained on an acceptable confidence level. Therefore, to be able to adopt these methods, a more sophisticated design is applied, leading to a poor appearance, bulkiness, and one or more physical constraints in a final design, all of which would in turn affect effectiveness and compliance of the devices. There are some designs embracing modern motion detection approaches that use accelerometers (or combined with gyroscopes), as in U.S. Pat. No. 6,984,208B2, US20110063114A and US20130108995A1. Using such type of sensors can acquire more reliable data inputs and enable more flexible designs. However, providing an efficient detection mechanism that fully utilizes such sensor readings is still a challenging issue. Especially in the area of posture correction, it is impossible to define an absolutely correct posture out of the measurement provided by the sensors. In this case, the naive feedback algorithm with a threshold-based detection algorithm that most existing works have proposed would not suffice.

Very limited feedback means have been adopted in existing techniques. Specifically, only sound and vibration are utilized in a form of alert (a.k.a. notification). However, as mobile devices such as smartphones and tablets have become increasingly pervasive, more user-friendly feedback means can be advantageously provided through those devices. To be more specific, feedback should not only limited to the form of alert, but integrated into existing mobile devices, providing progressive and tailored posture training to patient with AIS with a view to restore a balance in muscle activities and to reduce the displacement of both sides of the spine.

There is a need in the art to have improved methods and apparatus over existing ones as a treatment for AIS.

SUMMARY OF THE INVENTION

An exemplary embodiment of the present disclosure provides a biofeedback system for monitoring patient-related signals of a patient having adolescent idiopathic scoliosis (AIS), providing a personalized biofeedback to the patient based on the patient-related signals, and providing posture trainings to the patient by restoring a balance in muscle activities and reducing a displacement of both sides of the patient's spine as a treatment for AIS. The biofeedback system comprises (1) a garment integrated with posture monitoring sensors, and (2) one or more computational systems comprising a sensor-based sEMG posture training subsystem for providing posture training and a posture monitoring subsystem for providing progressive training through daily activities. Each posture monitoring sensor comprises a 3-axis accelerometer.

The sensor-based sEMG posture training subsystem comprises a posture training device, coupled to a plurality of sEMG sensors, for triggering a feedback device as a motivation program facilitating the patient to balance the muscle activities, and determining a calibration function for synchronizing the sEMG sensors with the posture monitoring sensors as a calibration for the posture monitoring sensors. The calibration function determines ranges of preferred patient-related signals when the posture training device determines that both sides of the patient's spine are balanced.

The posture monitoring subsystem comprises a mobile processor configured to be communicable with the posture monitoring sensors on the garment for aggregating the patient-related signals of the patient through daily activities and determining a properness of the posture; and to provide a real-time feedback to the patient on the properness of the posture.

In accordance with a further aspect of the present disclosure, the plurality of sEMG sensors further comprises four pairs in total of eight sEMG sensors cover full paraspinal muscle. The paired sEMG sensor are placed on a pair of paraspinal muscles of the patient for evaluating a myoelectric activity of the pair of paraspinal muscles quantitatively based on a concave sEMG signal and a convex sEMG signal respectively. The concave sEMG signal and the convex sEMG signal are used to determine a root-mean-square (RMS) sEMG ratio for indicating a symmetric level of the pair of paraspinal muscles based on:

$$\text{RMS } sEMG \text{ Ratio} = \frac{\text{RMS } sEMG(\text{convex})}{\text{RMS } sEMG(\text{concave})}$$

In accordance with a further aspect of the present disclosure, the RMS sEMG ratio is used to determine the visual feedback to the patient, and the patient adjusts the balance in muscle activities based on the visual feedback such that the RMS sEMG ratio can be as close to 1 as possible. The sEMG signals are filtered by one or more band pass filters and a notch filter.

In accordance with a further aspect of the present disclosure, the one or more posture monitoring sensors are positioned at locations proximate to T3, T12 and L4-L5 of the patient's spine. The posture monitoring sensors may include additional sensors including a gyroscope, and a temperature sensor. Each of the posture monitoring sensors further comprises a micro-controller unit (MCU) with a wireless communication interface.

In accordance with a further aspect of the present disclosure, the mobile processor is used for analyzing the patient's posture by comparing the aggregated patient-related signals through daily activities with the ranges of preferred patient-related signals.

In accordance with a further aspect of the present disclosure, the determining of the properness of the posture is implemented on a cloud infrastructure.

In accordance with a further aspect of the present disclosure, the posture monitoring system further comprises a database for storing the real-time data of the patient's posture through daily activities. The database is accessible by doctors or specialists for a long-term real-time surveillance on a progress of the patient.

In accordance with a further aspect of the present disclosure, the garment is fabricated as a body-mapping tank-top for accommodating the posture monitoring sensors on a posterior and medial part of the torso of body-mapping tank-top along the patient's spine.

In accordance with a further aspect of the present disclosure, the wireless communication interface is configured to support one or more communication protocols for communicating with the posture training device and the portable electronic device, the one or more protocols being selected from Bluetooth, Wireless Body Area Network (WBAN), including inter-integrated circuit (I2C), and serial (COM) communication.

In accordance with a further aspect of the present disclosure, the feedback device is a visual screen used for displaying an animation as the motivation program facilitating the patient to balance the muscle activities.

In accordance with a further aspect of the present disclosure, the mobile processor is a processor of a mobile device such as a smart-phone, a smart-watch, or a tablet, and controls a mobile application for providing the real-time feedback to the patient on the properness of the posture. The mobile application is designed to provide a visual summary with respect to the information obtained from the posture monitoring sensors for the patient to monitor, and the mobile application can be developed on one or more operation systems including iOS or Android.

DETAILED DESCRIPTION

The present disclosure relates generally to an adolescent idiopathic scoliosis (AIS) treatment. More specifically, but without limitation, the present disclosure relates to a sensor-based biofeedback system using a body mapping clothing for monitoring patient-related signals of a patient with AIS and thereby enabling the patient to obtain a dynamic, personalized biofeedback based on the patient-related signals, wherein the biofeedback is generated from a processor, a computer system, or a computing server, calibrated with surface electromyographic (sEMG) signals, and analyzed by the processor, the computer system, or the computing server for providing progressive and tailored posture training to patient with AIS.

The following detailed description, the system and the corresponding treatment methods are merely exemplary in nature and are not intended to limit the disclosure or its application and/or uses. It should be appreciated that a vast number of variations exist. The detailed description will enable those of ordinary skill in the art to implement an exemplary embodiment of the present disclosure without undue experimentation, and it is understood that various changes or modifications may be made in the function and arrangement of devices and methods of operation described in the exemplary embodiment without departing from the scope of the present disclosure as set forth in the appended claims.

In the specification and the appended claims, the term "cloud" is construed and interpreted in the sense of cloud computing or, synonymously, distributed computing over a network unless otherwise specified. "A server" as used herein is interpreted in the sense of computing. The one or more "database" may be, for example, electrical circuits, hard disks and/or other solid-state disks for storing data. Generally, a server is equipped with one or more processors for executing program instructions, and/or one or more storages for storing data. The server may be a standalone computing server, or a distributed server in the cloud.

Furthermore, as used herein, the term "scoliosis" refers to is a multi-factorial, three-dimensional deformity of the spine and trunk. Scoliosis can be classified into three main groups, namely, idiopathic, congenital or secondary to a neuromuscular disease. Idiopathic scoliosis is a structural spinal curve that occurs without a clear cause, which can further be classified by the first diagnosed age of the patients. Juvenile idiopathic scoliosis patients are first diagnosed between the ages of 4 to 10 years old, while adolescent idiopathic scoliosis (AIS) patients are first diagnosed between the ages of 10 to 15 years old with skeletal maturity. The focus of the present disclosure is on AIS, which is the most common form of scoliosis.

Figure 3:
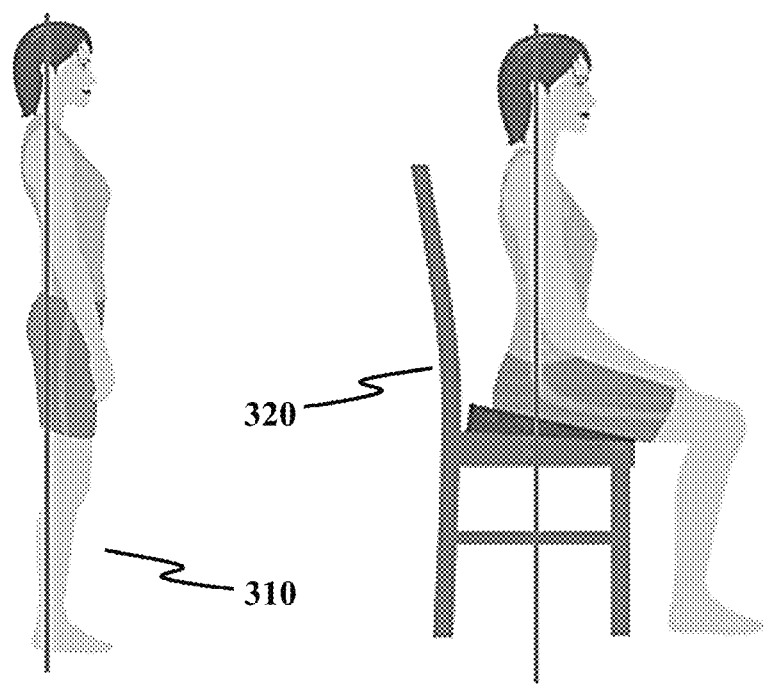
FIG. 3 depicts an exemplary good standing posture and an exemplary good sitting posture.

The term "posture", as used herein, refers to the orientation or alignment of body segments with respect to the balance of the muscle activities when maintaining an upright position. When a "good posture" is referred to, it is intended that the state of muscular and skeletal balance can protect the body structure against injury or progressive deformity, while a "poor posture" is referred to any prolonged deviation from a neutral spine. FIG. 3 demonstrates an exemplary good standing posture 310 and an exemplary good sitting posture 320. As proposed by McKenzie (1980) [1], the recommended standing position is that the head and ankles are to be straight, shoulders and hip are level, kneecaps face the front, head and knees are straight, and the chin should be parallel to the floor and aligned with the ears. The lower back is slightly bent forward with the aid of the chest, stomach and buttock muscles. On the other hand, the recommended sitting position is that the head and ankles are to be straight, shoulders and hips are level, kneecaps face the front and the chin should be parallel to the floor and aligned with the ears. The lower back is slightly bent forward to support the body with no extra weight distributed onto the spine.

Figure 4:
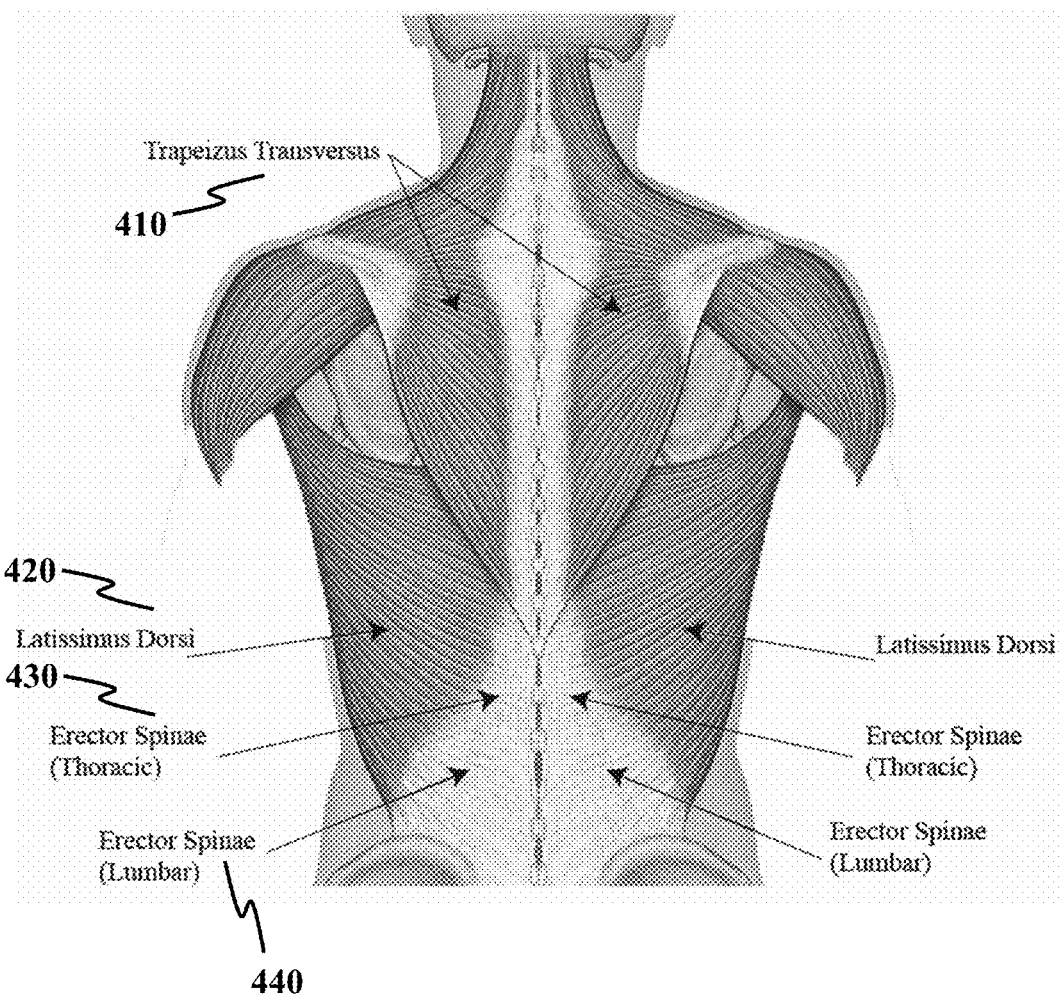
FIG. 4 is a superficial view of the back muscles depicting the targeted muscles regions for sEMG testing.

The present disclosure aims to develop an innovative sensor-based biofeedback system using a body-mapping garment, in a preferred form of a tank-top, for adolescents with early scoliosis. Advantageously, the biofeedback system is equipped with a plurality of 3-axis accelerometer sensors that synchronized with the sEMG signals. Specifically, the term "biofeedback", as used herein, refers to a method of training in medicine and psychology which enables a person, mostly with the help of electronic equipment, to learn to control otherwise involuntary bodily functions. Therefore, the biofeedback system provides muscle re-education at specific areas, including the upper trapezius, thoracic and lumbar regions as shown in FIG. 4, so as to strengthen muscle strength and train the individual into adapting the desired good posture during sitting and standing, which is very useful for prevention and/or controlling of the curve progression of spinal deformities.

Particularly, the present disclosure provides a compact, non-intrusive wearable posture monitoring subsystem to provide a real-time data surveillance, notification, and motivational posture monitoring program for the patients through their daily activities and exercises. Via long-term and continuous use, the system can deliver analysis and intervention techniques that used to be only available inside institute/laboratory environment. By participating in one or more sEMG posture trainings, a calibration function can be obtained for synchronizing the data of the sensors with the sEMG signals. Preferably, the sEMG posture training is feedback triggered by the measured sEMG signals for motivating the patient to adapt a good and more balanced posture when sitting by reducing the difference between the sEMG signals on the left and right sides of the same pair of muscles. The calibration function can calibrate the 3-axis accelerometer sensors for determining the reference data of the sensors when the posture is good. The mobile applications developed for monitoring the data of the sensors during daily activities can encourage the patient to maintain balance in their muscle activities. All the data acquired from the mobile device and the sEMG posture training can be further provided to doctors or specialists in a timely manner.

As is mentioned above, the naive feedback algorithm with threshold based detection that most of the existing works employ does not suffice. The present disclosure mitigates this shortcoming by involving a calibration mechanism between the sEMG signals and the data from the 3-axis accelerometer sensors, to achieve an adaptive and personalized feedback. The calibration mechanism may also combine and process information on the patient's behavior pattern, expert knowledge (doctor's diagnostic opinion, instructions, etc.), and predefined profiles created by the patient and/or doctor. As a result, more accurate, dynamic and personalized feedback can be provided to the patient. Besides the diagnostic surveillance and posture correction in the patient's daily activities, the system in the present disclosure is also utilizable to progressively facilitate customized muscle training to the patient with scoliosis so as to restore a balance in muscle activities and reduction in the displacement of both sides of the spine.

In short, the present disclosure is concerned with a sensor-based biofeedback system for patients with AIS, in which real-time data about a patient's posture, motion and muscle activities are recorded, stored in both local and cloud-based databases and analyzed to determine the properness of the posture. Patients can receive tailor-made sensor-based sEMG posture trainings which involve restoration of muscle balance, with an aim to determine a calibration function for facilitating a posture monitoring program for the patients through their daily activities such that the patient can play an active role in improving their control and coordination of movement and daily posture more efficiently.

The present invention is illustrated according to an exemplary design of the biofeedback system as disclosed in Section A. The advantages thereof are elaborated in Section B, while the trial test results are detailed in Section C.

A. An Exemplary Design of the Biofeedback System

The biofeedback system of the present disclosure comprises (1) a garment integrated with one or more posture monitoring sensors, and (2) one or more computational systems, wherein the one or more computational systems comprises a sensor-based sEMG posture training subsystem for providing posture training and a posture monitoring subsystem for providing progressive training through daily activities.

Figure 1:
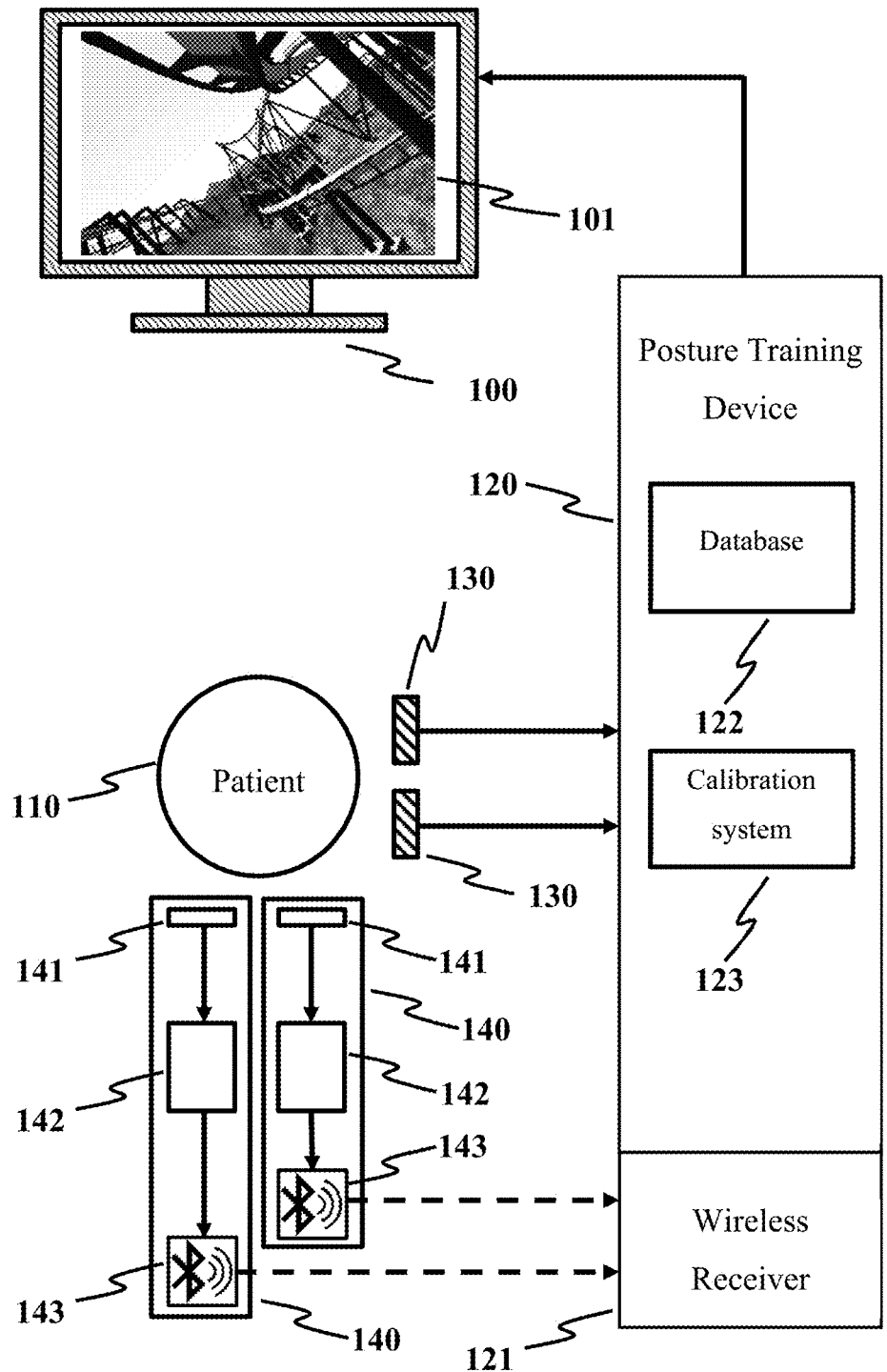
FIG. 1 is a conceptual diagram depicting the sensor-based sEMG posture training subsystem in accordance with an exemplary embodiment of the present disclosure.

FIG. 1 is a conceptual diagram depicting the sensor-based sEMG posture training subsystem. The sEMG posture training subsystem for training a patient 110 comprises a posture training device 120, one or more sEMG sensors 130, one or more posture monitoring sensors 140 and a visual display 100. The system incorporates sEMG signals and 3-axis accelerometers data for posture detection. Each posture monitoring sensor 140 further comprises a 3-axis accelerometer sensor 141, micro-controller unit (MCU) 142 equipped with a Bluetooth transmitter 143, a thermometer, a gyroscope, and a battery. The posture monitoring sensors 140 are wearable components which can be integrated in a garment. Real-time data about a posture, a motion, etc. of the patient 110, as well as other vital signal thereof such as body temperature are recorded by the posture monitoring sensors 140, transmitted to the posture training device 120, which can be a personal computer with a training software or a customized electronic device, via wireless receiver 121, stored in databases 122 (local and/or cloud-based server) and synchronized with the sEMG signals from the one or more sEMG sensors 130 for determining the muscle activities of the patient 110. The posture training device 120, which can be a processor, or a computation system implemented by a personal computer, cloud-based server, or other electronic devices capable of performing computation, controls a feedback device for providing real-time information to the patient in relation to his/her posture, preferably the feedback device is implemented by a visual display 100 playing an animation 101 as a feedback to the patient 110 based on the sEMG signals and/or other real-time patient-related signals. The feedback is a motivation program facilitating the patient 100 to balance the muscle activities with a proper posture.

Figure 2:
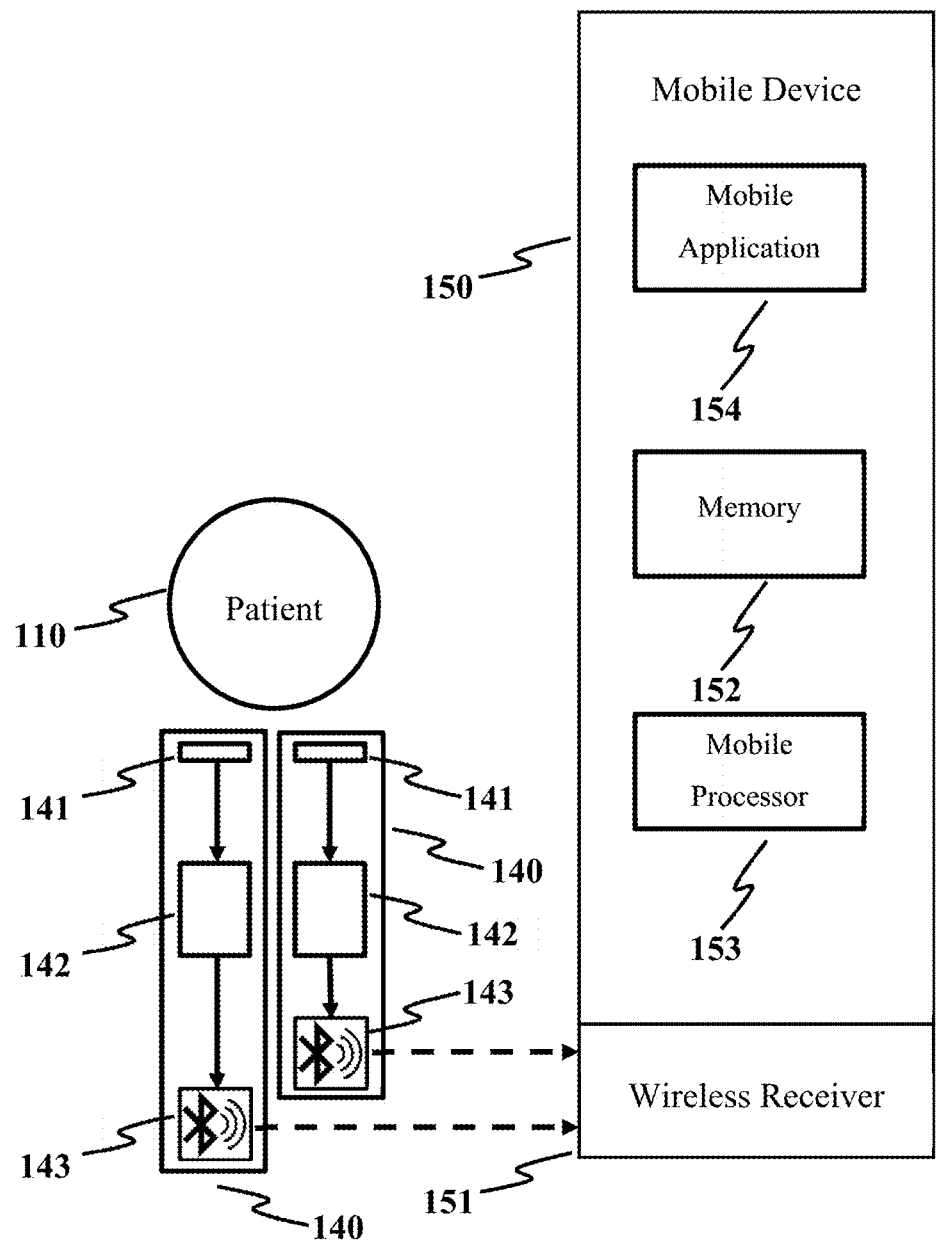
FIG. 2 is a conceptual diagram depicting the posture monitoring subsystem in accordance with an exemplary embodiment of the present disclosure.

FIG. 2 is a conceptual diagram depicting the posture monitoring subsystem. The subsystem for providing real-time data surveillance, notification, and motivational posture monitoring program to patient 110 through their daily activities comprises one or more posture monitoring sensors 140 and a mobile device 150. The posture monitoring subsystem uses the same or similar posture monitoring sensors 140 as the sEMG posture training subsystem. Preferably, the posture monitoring sensors 140 are integrated in a garment such that the daily activities can be effectively monitored. Real-time data about a posture, a motion, etc. of the patient 110 through daily activities, as well as other vital signal thereof such as body temperature are recorded by the posture monitoring sensors 140, transmitted to the mobile device 150 via wireless receiver 151, stored in a memory 152 (local and/or cloud-based server) and analyzed by a mobile processor 153. The mobile device 150 can be any portable electronic devices, for example: smart-phone, smart-watch, tablet, personal digital assistant (PDA), laptop, or other electronic device with one or more microcontrollers that can easily be carried along with. The mobile processor 153 can be a processor or a computation system of the mobile device 150 capable of performing computation. In one embodiment, the computation can be performed by the mobile processor 130 and/or other cloud-based processors. A mobile application 154 is designed to provide visual summary regarding the information obtained from the posture monitoring sensors 140 such that the patient 110 can monitor the posture through his/her daily activities.

A.1. Posture Monitoring Sensor

The posture monitoring sensor 140 used in the design contains, but not limited to: a 3-axis accelerometer 141, a gyroscope, and a temperature sensor. The sensors are connected to a MCU 142 equipped with a Bluetooth transmitter 143. Preferably, the architecture of the posture monitoring sensor 140 is extremely concise (minimalistic) and light such that the daily activities is not affected or limited after using the posture monitoring sensor 140. An exemplary device developed is circular in shape with a diameter of 3 cm. A 3V battery is embedded which allows the system to operate continuously for more than a day without charging or replacing the battery.

The MCU 142 in the posture monitoring sensor 140 is used for processing the sensed data. A filtering function is programmed directly into and executed by the MCU 142, such that the MCU 142 can provide real time monitoring functions by simultaneously correlating the sensed data with the body posture. The real-time data recorded can be provided to the posture training device 120 or mobile device 150 through Bluetooth. The transmission can also be implemented by other wireless communication method including Wireless Body Area Network (WBAN), or other wired connections including inter-integrated circuit (I²C), and serial (COM) communication. Caching techniques may also be adopted to guarantee smooth data transmission.

The MCU 142 is programmable, and the code executed in the MCU 142 needs to guarantee compatibility among different models of posture training device 120 or mobile device 150. In addition, an upgrade feature may be provided to guarantee forward compatibility when major changes on any access protocol have been made.

The positioning of the posture monitoring sensor 140 may be different for each patient 110. Generally for patients with AIS, the sensors are placed along the spinal cord for monitoring the posture. With reference to the superficial view of the back muscles as shown in FIG. 4, the Trapezius Transversus 410, Latissimus Dorsi 420, Erector Spinae (thoracic) 430 and Erector Spinae (lumbar) 440 regions are of particular importance for maintaining a balanced posture. Therefore, three posture monitoring sensors 140 are placed at location T3 for monitoring the thoracic torso, location T12 for monitoring the thoracolumbar spine and location L4-L5 for monitoring lumbar spine respectively. Three rectangular shaped pockets 201 are fabricated on the back of the body mapping garment 200 along the spinal cord position to hold the sensors in place.

Patients who tend to move their thoracic spine forward, which could potentially result in a hunch back, will be detected by the first sensor located at T3. The second sensor positioned at T12 can measure the thoracolumbar spine position by using the 3-axis accelerometer sensor 141 strapped at the pelvis over the sacrum, ribcage and T12. The third sensor placed at location L4-L5 can measure the muscle activities in the lumbar region.

The three posture monitoring sensors 140 are preferably placed at the aforesaid positions, but may vary depending on the individual medical conditions of the patient 110 in terms of the position and the number of sensors. Therefore, it will be apparent to those skilled in the art that such variations may be possible without departing from the scope and spirit of the present disclosure.

A.2. Body Mapping Clothing

A body mapping garment 200, preferably in the form of a tank-top, or other clothing capable of equipping with one or more posture monitoring sensors 140 is developed in the present disclosure. The body mapping garment 200 itself does not have the ability to monitor the posture of the patient 110. Therefore it is important to accommodate the posture monitoring sensors 140 into the body mapping garment 200 so as to develop a complete apparatus for monitoring the posture of the patient 110.

Figure 5:
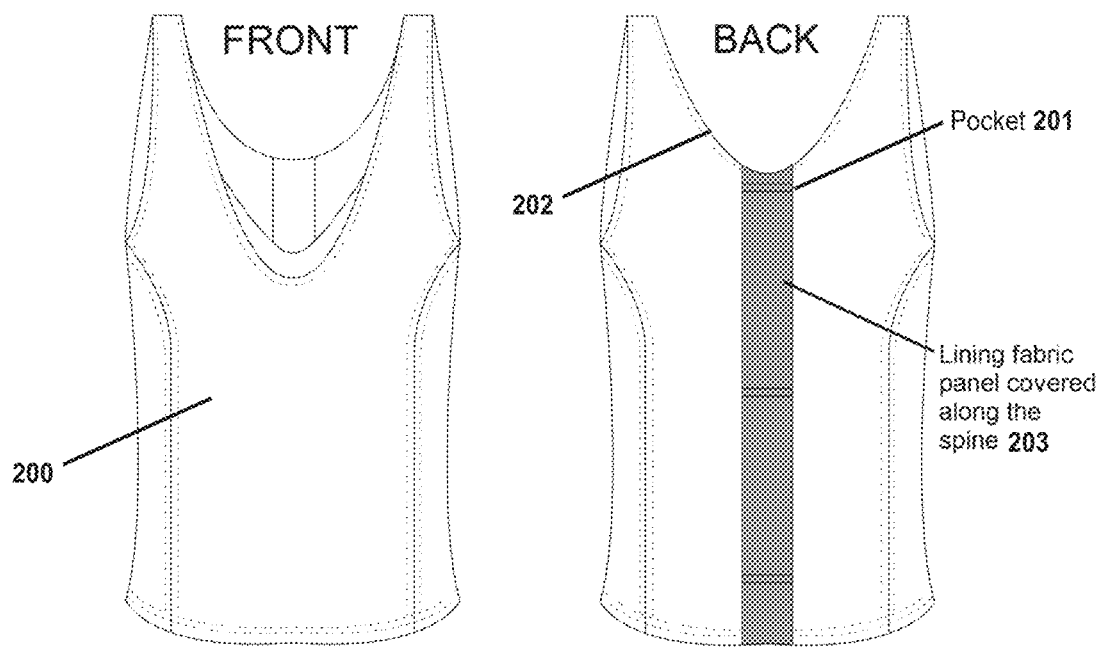
FIG. 5 shows various views of an exemplary production of the body mapping tank-top in accordance with an exemplary embodiment of the present disclosure.
Figure 5:
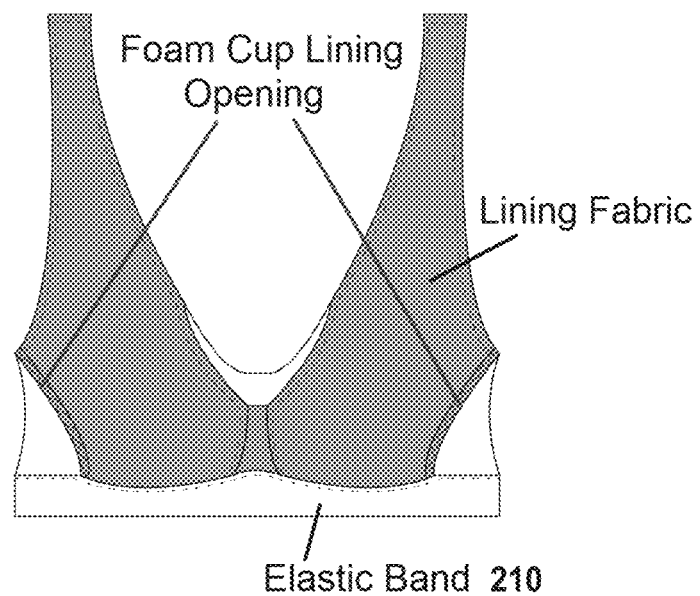
Figure 6:
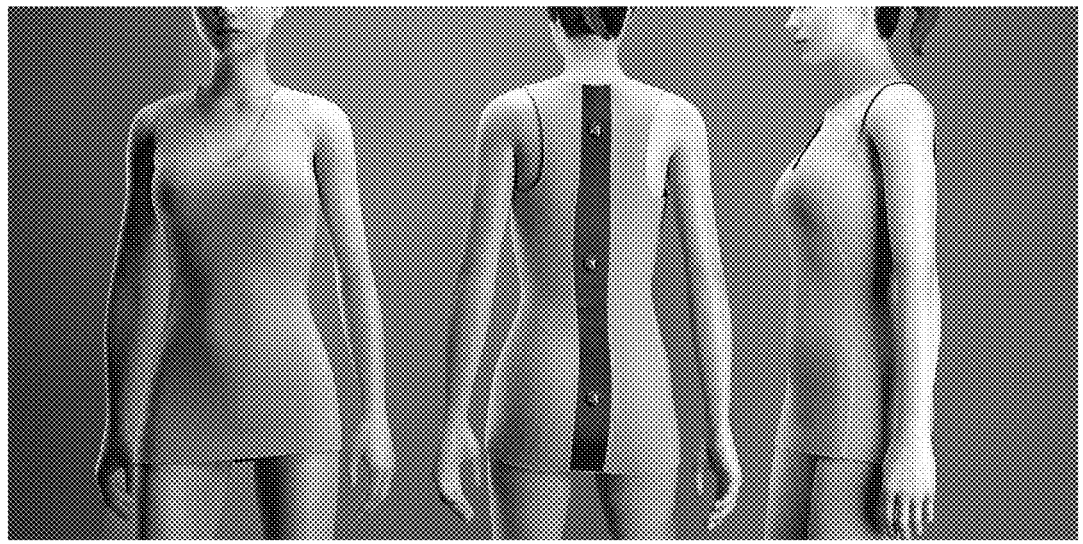
FIG. 6 is a 3-dimensional illustration of the body mapping tank-top according to FIG. 5.

The production drawing of the body mapping garment 200 is shown in FIG. 5, and the 3-dimensional illustration of the body mapping garment 200 is shown in FIG. 6. The body mapping garment 200 serves two main purposes: First, it is designed to accommodate the posture monitoring sensors 140 and secure their positioning. Second, it should be a very comfortable garment for the patient 110. From the front and back views in FIG. 5, U-shaped shoulder straps 202 with a width of 1 inch are placed on the back of the tank-top, which provide a continuous piece that extends from the front to the back of the garment. The U-shaped shoulder straps 202 provide the functions of exerting a pulling force to secure the body mapping garment 200 in place, and maximizing the cooling effect by reducing the fabric coverage on the back. The body mapping garment 200 also has a panel of powernet fabric (lining fibric) 203 on the posterior and medial parts of the torso along the spine and around the chest area. The excellent air permeability of the powernet fabric 203 allows these high sweat rate regions to stay relatively cool. As the one or more posture monitoring sensors 140 are placed along the paraspinal muscle position of the patient 110, therefore there are one or more pockets 201 fabricated on the back side of the body mapping garment 200 for holding the sensors, preferably along the powernet fabric 203 at location T3 for monitoring the thoracic torso, location T12 for monitoring the thoracolumbar spine and location L4-L5 for measuring the muscle activities in the lumbar region.

From the front interior view in FIG. 5, the body mapping garment 200 has a lining in the chest area in which a pair of thin foam paddings can be inserted for increased support of the breasts. The elasticity of the fabric for the foam cup lining is adequate enough to accommodate different foam thickness and size. This design feature allows an adolescent girl to wear this body mapping garment 200 as an undergarment and no further intimate apparel or bra is required. Therefore, the sensors can be positioned closer to the skin. The bottom of the lining is attached with an elastic band 210 for more support. Alternative design of the body mapping tank-top 200 without lining may be developed for an adolescent boy.

The body mapping garment 200, equipped with one or more posture monitoring sensors 140 can provide diagnostic surveillance and posture correction in the patient's daily activities, as a treatment for patients with AIS 110, who can be progressively trained to correct the posture through daily activities so as to restore the balance in muscle activities and reduce the displacement of both sides of the spine. Further details of the posture monitoring subsystem are disclosed in section A.5 below.

A.3. sEMG Sensor

The sEMG sensors 130 are electrodes placed on the skin overlying a muscle to detect the electrical activity of the muscles. This is a non-invasive method to analysis the myoelectric activities in the muscles of a patient 110.

For the purpose of the present disclosure, the sEMG sensors 130 in the sensor-based sEMG posture training subsystem are placed at the left and right sides of each pair of muscles of the patient 110. In one embodiment, there are totally eight sEMG sensors 130 placed on the back muscles alone the spine, with two sEMG sensors 130 at each of the Trapezius Transversus 410, Latissimus Dorsi 420, Erector Spinae (thoracic) 430 and Erector Spinae (lumbar) 440 regions. The signals obtained are transmitted to the posture training device 120 for determining the properness of the posture and synchronization with the data from the posture monitoring sensor 140.

A.4. sEMG Posture Training Subsystem

The sEMG posture training subsystem is a biofeedback system for providing sEMG posture training for a patient with AIS 110 and for synchronizing the 3-axis accelerometer 141 with the sEMG sensors 130. The training aims to encourage the patient 110 to balance their muscle activities with less effort by narrowing the difference between the sEMG signals on the left and right sides of the same pair of muscle regions, and reduce the overall sEMG signal values. The system examines the data from the sEMG sensors 130 and the posture monitoring sensors 140 as acquired from the patient 110, for determining whether the posture is good or not.

Figure 7:
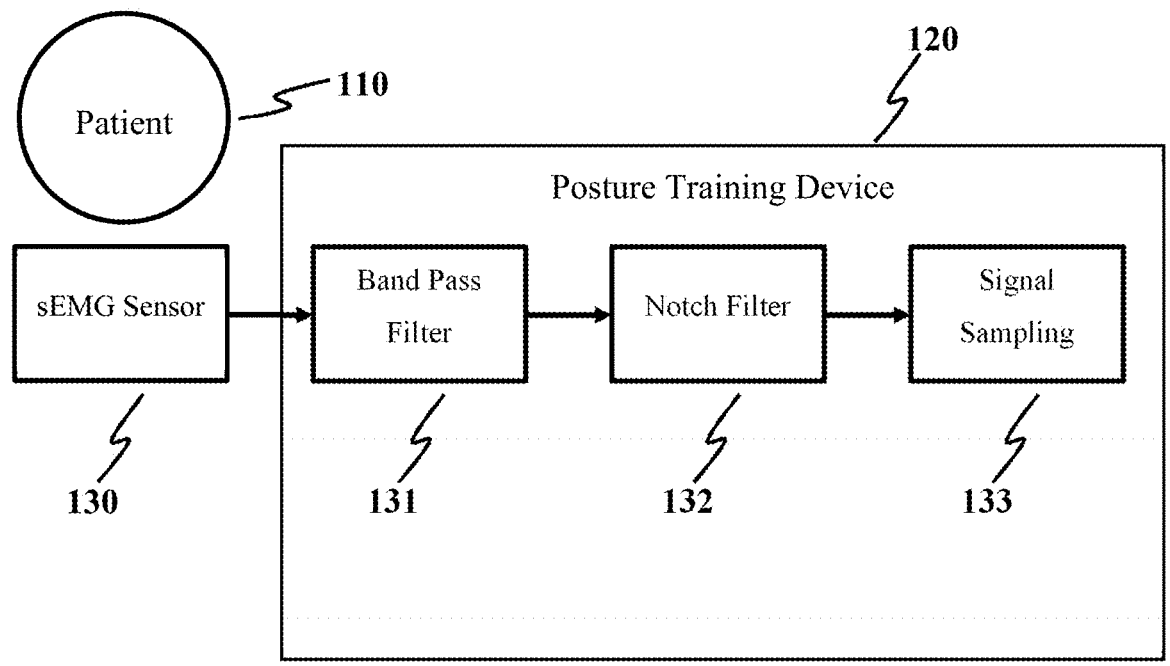
FIG. 7 is a conceptual diagram depicting the filtering and sampling system for the sEMG signals according to FIG. 1.

FIG. 7 illustrates the filtering and sampling system for the sEMG signals in the posture training system. Advantageously, the measurements by the sEMG sensors 130 with respect to the muscle activities of the paraspinal muscles of the patient 110 are evaluated quantitatively during each session of sEMG posture training. The acquired data is then filtered by one or more band pass filters 131 that ranged from 10 to 500 Hz for eliminating undesired artifacts, such as sudden bodily movement, and a 50 Hz or 60 Hz notch filter 132 for eliminating the noise due to coupling with the AC mains. Preferably, the resulting filtered sEMG signals are sampled at a rate of 2048 Hz 133. Root-mean-square (RMS) values of the sEMG signals were derived from each session of sEMG posture training. The RMS sEMG ratio of the patient 110 can be calculated based on the following equation:

$$\text{RMS } sEMG \text{ Ratio} = \frac{\text{RMS } sEMG(\text{convex})}{\text{RMS } sEMG(\text{concave})} \quad (1)$$

The RMS sEMG ratio is an index of the symmetric sEMG activity of the tested muscles, which when the ratio is 1, the tested muscle pairs have identical sEMG activity from the concave and convex sides of a tested muscle. If the RMS sEMG ratio is less than 1, the concave side of the muscle has a stronger sEMG activity than the convex side. If the RMS sEMG ratio is larger than 1, the concave side of the muscle has weaker sEMG activity than the convex side. Equation (1) is applied to assess the level of symmetrical muscle activities for determining whether the posture is good or not. The mean RMS sEMG ratio is a good index for indicating the level of symmetrical muscle activities during the sitting posture. The patient 110 should ideally obtain a RMS sEMG ratio of 1 in which the left and right sides of the same muscle region have perfectly symmetrical muscle activities.

With the purpose of training the patient 110 to adapt a more balanced posture, the patient 110 is encouraged to adjust the posture such that the RMS sEMG ratio is as close to 1 as possible. In the present disclosure, biofeedback is introduced in the sEMG posture training.

The biofeedback aims to encourage the patient 110 to balance each pair of muscles by narrowing the difference between the sEMG signals on the left and right sides of the same pair of muscles. Preferably, there are four pairs of sEMG sensors 130 placed bilaterally at Trapezius Transversus 410, Latissimus Dorsi 420, Erector Spinae (thoracic) 430 and Erector Spinae (lumbar) 440 regions for measuring the electrical activities of the muscles at the Trapezius Transversus 410, Latissimus Dorsi 420, Erector Spinae (thoracic) 430 and Erector Spinae (lumbar) 440 regions. The visual display 100 is controlled by the posture training device 120 as triggered by the sEMG signals and/or other real-time patient-related signals. The properness of the posture is presented to the patient 110 on the visual display 100 as a feedback. The feedback is a motivation program facilitating the patient 100 to balance the muscle activities with a proper posture. In one exemplarily embodiment, an animation 101 is played on the visual display 100 as the motivation program for the patient to balance the muscle properly. When the posture of the patient 110 is good, the animation is played continuously. However, the animation 101 is paused when the posture of the patient 110 is not good. The patient 110 is encouraged to adjust the posture and relax the muscles so that the animation 101 can be played continuously. Other motivation program may be used by indicating to the patient 110 on the properness of the posture, for example, by other graphical presentations or sound effect. The properness of the posture is determined according to the sEMG ratio as calculated by equation (1). There is an acceptable variation from the ideal balance ratio of 1 for equation (1), and the thresholds of the desired sEMG ratio, considering the acceptable variation, can be adjusted during the sEMG posture training, which further correlated to the posture monitoring sensors 140 for determining ranges of preferred patient-related signals when the muscles are balanced. Further optimization on the thresholds can also be performed by the calibration system 123 in accordance with the data acquired from the posture monitoring sensors 140, as well as the patient's behavior pattern, medical or physiological instructions from doctors or specialist, predefined profiles created by the patient and/or doctor, previous measurement data from database 122 (local and/or cloud-based server), and the overall progress trend of the patient 110, such that a knowledge-driven information can be used to determine the properness of the posture. The calibration system 123 can be implemented on mobile device 150 or on the cloud infrastructure. By using the thresholds from the sEMG posture training to determine the ranges of preferred patient-related signals of the posture monitoring sensors 140, it is feasible to break the barrier due to using conventional naive feedback and threshold-based detection algorithms, thus providing more accurate, dynamic and personalized feedback means for the patient 110.

In one embodiment, the sEMG posture training subsystem provides the patient 110 with at least 30 training sessions. The duration of each session is around 50 minutes. Each session includes a sEMG preparation period, a baseline data checking, five iterations of 5-minute posture trainings using the sEMG posture training subsystem, and a session summary. This procedure was used in the trial test as disclosed in the section C below. It should be understood that various changes, substitutions and alterations to the arrangement of the training session can be made without departing from the spirit and scope of the present disclosure.

Furthermore, the present disclosure of the sEMG posture training subsystem also provides a calibration of the posture monitoring sensor 140. The real-time data obtained from the posture monitoring sensor 140 can be synchronized with the measurements by the sEMG sensors 130 with respect to the muscle activities. As the posture training device 120 can determine the properness of the posture based on the sEMG signals, the corresponding real-time data from the posture monitoring sensor 140, when the sEMG ratio is within the thresholds, can also be obtained. This can help to identify a calibration function, which is a key element for synchronizing the data of the posture monitoring sensor 140 with the data obtained by sEMG sensors 130 during the sEMG posture training. As mentioned above, the sEMG posture training is featured with a feedback as triggered by the sEMG signals. The posture monitoring sensors 140 are synchronized through the sEMG signals which calibrate the posture monitoring sensors 140 at that time. The preferred ranges of data for the 3-axis accelerometer sensors 141 can be determined, defining the required data of the posture monitoring sensors 140 for good posture in the subsequent posture monitoring subsystem. The calibration function, preferred ranges of data for the 3-axis accelerometer sensors 141 and/or other data aggregated by the sEMG posture training subsystem can be stored in the memory 152 of the mobile device 150. Therefore, the patient can easily reference to and be restricted to a similar posture during posture monitoring through daily activities with mobile device 150.

A.5. Posture Monitoring Subsystem

As a treatment for patients with AIS 110 in accordance with the present disclosure, the posture monitoring subsystem can progressively train the patient 110 to correct the posture through daily activities, in accordance with the data from the 3-axis accelerometer sensors 141 as determined and calibrated during the sEMG posture training, so as to restore the balance in muscle activities and reduce the displacement of both sides of the spine. Therefore in the second stage of the biofeedback system, a posture monitoring subsystem with a mobile device 150 is introduced.

In the mobile device, a mobile application 151 is developed to provide visual information of the data obtained from the posture monitoring sensors 140. The mobile application 151 can be developed for different operation systems, including iOS or Android, and supports communication to the posture monitoring sensors 140 with Bluetooth or other wireless communication interfaces. In one embodiment, the mobile application 151 can connect and display the information of the 3 posture monitoring sensors 140 at the same time. Real-time patient-related signals about a posture, a motion, etc. of the patient 110 through daily activities, as well as other vital signal thereof such as body temperature, atmosphere temperature, body posture angle, battery level and calibration function are aggregating by the posture monitoring sensors 140, transmitted to the mobile device 150 via wireless receiver 151, stored in a memory 152 (local and/or cloud-based server) and analyzed by the mobile processor 153 and/or other processors on the cloud infrastructure.

Data representation, evaluation, and optimization are performed based on the data acquired from the posture monitoring sensors 140, as well as the medical or physiological instructions from doctors or specialists, sEMG data from the sEMG posture training, previous measurement data from database 122 (local and/or cloud-based server), and the overall progress trend of the patient 110, such that a knowledge-driven information can be used to determine the properness of the posture and to provide a tailored posture training to the patient 110. The results can be presented to the patient 110 using the mobile application 151, and can also be synchronized to the cloud so that doctors or specialists can access the long-term real-time surveillance patient-related signals of the patient 110.

In one embodiment, the mobile processor 153 aggregates the patient-related signals of the patient through daily activities and analyzes the patient's posture by comparing the aggregated patient-related signals from daily activity with the ranges of preferred patient-related signals as determined by the calibration system 123 of the sensor-based sEMG posture training subsystem. Therefore, the patient 110 can be restricted to postures where the myoelectric activities of the muscle pairs are balanced.

The present disclosure may be embodied in other specific forms without departing from the spirit or essential characteristics thereof. The present embodiment is therefore to be considered in all respects as illustrative and not restrictive. The scope of the disclosure is indicated by the appended claims rather than by the foregoing description, and all changes that come within the meaning and range of equivalency of the claims are therefore intended to be embraced therein.

B. Advantages of the Biofeedback System Over Existing Methods

The biofeedback system as disclosed above has several advantages over existing ones.

1. Conventional brace is bulky and uncomfortable. The system is realized in a form a garment, offering comfort to the patient.

2. Many existing diagnostic approaches are conducted in hospital/laboratory environment. A doctor or a specialist cannot acquire long-term real-time diagnostic surveillance data from the patient. On the other hand, the system as disclosed above enables remote monitoring of the patient through daily activities. The data from the posture monitoring sensors 140 can be used by the doctor or the specialist to perform diagnosis.

3. In conventional approaches, data analysis and intervention techniques can only be provided in a hospital/laboratory environment. Diagnostic results cannot be delivered to the patients promptly whenever the patient needs them. The system disclosed above, on the other hand, enables prompt delivery of the results from the sEMG posture training to the mobile device 150 of the patient 110.

4. Other existing posture training devices use simple feedback (normally audio/vibration alert), rather than the use of a biofeedback with an interactive feedback.

5. Other existing biofeedback devices use the threshold-based detection, lacking the ability to provide dynamic, personalized and adaptive feedbacks.

6. In the conventional biofeedback system design, the computation logic is mainly achieved on a MCU of the sensor device. It consumes a lot of power as the computation involved is complicated, so that the battery-support time of this conventional design is considerably short. Different from the conventional biofeedback system design, the system as disclosed above perform the computation on mobile device 150, cloud infrastructure, or posture training device 120, which are all possess better computational capacity. Therefore, the computational power required by the posture monitoring sensors 140 is reduced and thereby lengthens the battery-support time provided.

C. Trial Test Result

The performance of the biofeedback system in accordance with the present disclosure was evaluated under a trial test scheme, carried out in Hong Kong, China. A screening test was first performed to identify students with AIS. A group of female students aged 10 to 13 were invited to perform the Adam's forward bending test as a pre-screening test, and an OSI scoliometer for measuring the angle of trunk inclination (ATI) in the spine of the each student while lying prone, in order to preliminarily assess their spinal conditions. Amount them, 17 students (hereinafter referred to as "subjects") were identified as potential AIS patients, with curve angles above 10 degrees and without any previous surgical or orthotic treatment for AIS. They were recruited for the preliminary examination.

Curve type can be defined on the basis of the guidelines of the Peking Union Medical College (PUMC) classification system. The subjects were therefore divided into 3 groups based on this system: PUMC Type Ia with a single curve where the thoracic apex is between the T2 and T11-T12 discs; PUMC Type Ic with a single curve where the lumbar apex is between the L1-L2 and L4-L5 discs; and PUMC Type IIc with both a thoracic curve and a thoracolumbar/lumbar curve, where the curve difference is less than 10°. The demographic data of the subjects are shown in Table I below.

TABLE I

Demographic data of the subjects as classified by PUMC Type

| PUMC Type | Convex Side | N | Curve angle (°) | Mean (S.D.) |
|---|---|---|---|---|
| Ia | Right (Thoracic) | 5 | Height (cm) | 155.4 (4.454) |
| | | | Weight (kg) | 48.16 (4.192) |
| | | | Thoracic Curve Angle (°) | 16.30 (6.697) |
| | | | Lumbar Curve Angle (°) | N/A |
| Ic | Left (Lumbar) | 2 | Height (cm) | 155.5 (0.500) |
| | | | Weight (kg) | 39.15 (2.050) |
| | | | Thoracic Curve Angle (°) | N/A |
| | | | Lumbar Curve Angle (°) | 17.30 (4.300) |
| IIc | Right (Thoracic) Left (Lumbar) | 10 | Height (cm) | 150.9 (4.989) |
| | | | Weight (kg) | 42.10 (7.234) |
| | | | Thoracic Curve Angle (°) | 16.14 (5.830) |
| | | | Lumbar Curve Angle (°) | 16.13 (3.233) |

C.1. sEMG Assessment Before Training (Preliminary Examination)

The parameters of the sEMG assessment were formulated based on the methods provided above. During the collection of the sEMG data for habitual standing, the subjects were barefoot with arms relaxed and lightly clasped in front of their body and feet positioned 20 cm apart. Under standardized instructions, the subjects were positioned by the same investigator for all of the trials. They were instructed to focus straight ahead and look at a designated point. The habitual posture is the natural posture performed without any instructions from the physiotherapist. A treatment chair with adjustable height was used for all of the habitual sitting positions. The hips and knees were flexed to 90°. Subsequently, the subjects were instructed to perform the suggested standing and sitting postures. The suggested positions as guided by the physiotherapist aimed to retain their postural balance during standing and sitting, which are considered to be common daily positions. By restricting the scoliotic adolescents to maintaining a balanced posture, the paraspinal muscles of the two sides are able to achieve a more balanced state.

Table II shows the mean of the RMS sEMG ratio of the paraspinal muscles of the subjects during habitual standing and sitting, and suggested standing and sitting positions. The items highlighted with ampersand (&) indicate posture improvement under the guidance of the physiotherapist, in which the RMS sEMG ratios of the suggested positions are closer to 1 as opposed to that obtained by the same habitual posture.

TABLE II

The mean RMS sEMG Ratio at habitual and suggesting posture

| PUMC Curve Type | N | Muscle Region | Mean RMS sEMG Ratio (S.D) | | | |
|---|---|---|---|---|---|---|
| | | | Habitual Standing | Suggested Standing | Habitual Sitting | Suggested Sitting |
| Ia | 2 | Trapezius | 1.15 | 0.65 | 1.01 | 0.69 |
| | | Transversus | (0.09) | (0.37) | (0.17) | (0.27) |
| | | Latissimus Dorsi | 0.99 (1.09) | 1.55 (1.45) | 0.58 (0.54) * | 0.96 (0.56) * |
| | | Erector Spinae (Thoracic) | 0.60 (0.70) | 0.60 (0.71) | 0.37 (0.40) * | 0.47 (0.40) * |
| | | Erector Spinae (Lumbar) | 0.90 (0.59) | 1.21 (0.14) | 0.40 (0.21) | 0.67 (0.40) & |
| Ic | 2 | Trapezius | 1.07 | 0.59 | 0.81 | 1.18 |
| | | Transversus | (0.87) | (0.62) | (0.52) | (0.74) & |
| | | Latissimus Dorsi | 1.13 (0.21) | 0.87 (0.23) | 1.03 (0.08) | 0.72 (0.32) |
| | | Erector Spinae (Thoracic) | 1.29 (0.74) | 0.72 (0.29) & | 2.21 (0.96) | 0.95 (0.12) & |
| | | Erector Spinae (Lumbar) | 0.64 (0.77) | 0.73 (0.18) & | 0.85 (0.88) | 0.78 (0.62) |
| IIc | 6 | Trapezius | 2.45 | 1.67 | 1.94 | 1.46 |
| | | Transversus | (1.96) | (0.89) & | (1.90) | (0.85) & |
| | | Latissimus Dorsi | 0.71 (0.43) | 0.88 (0.50) & | 0.74 (0.40) | 1.10 (0.64) & |
| | | Erector Spinae (Thoracic) | 1.14 (1.20) | 0.65 (0.39) | 1.18 (1.35) | 0.72 (0.47) |
| | | Erector Spinae (Lumbar) | 1.12 (0.84) | 0.89 (0.76) & | 1.56 (1.25) | 0.81 (0.43) & | a. Items marked with ampersand (&) indicates a more balanced mean RMS sEMG Ratios
b. Items marked with asterisk (*) are those statistical significance ($p < 0.05$)

From the above results, it is shown that the subjects with PUMC type Ia, with a single curve at the thoracic region, benefit relatively more from the suggested sitting positions. During the suggested sitting position, they are able to achieve a more balanced RMS sEMG ratio (closer to 1) at the latissimus dorsi, erector spinae thoracic and erector spinae lumbar regions as opposed to when they are in their habitual sitting posture. A paired student t-test was conducted. The t-test is a statistic method for evaluating whether the mean difference between two sets of data is zero. By a null hypothesis in the analysis, it is assumed that the mean difference between habitual and suggested posture is zero. The statistical significant difference between habitual and suggested sitting for PUMC type Ia subject was found. The p-value at latissimus dorsi and erector spinae thoracic regions was $p=0.032$ and $p=0.004$ respectively (marked with asterisk). As the p-value are both smaller than 0.05, the null hypothesis is rejected and it is concluded that there is a statistical significance between habitual and suggested sitting posture, and single curve patients with idiopathic scoliosis benefit most during static exercise. During the suggested sitting position, the RMS sEMG ratio is closer to 1 at some tested muscle regions versus the habitual sitting posture for other curve type participants.

It is important to note that the convex side where the spinal deformity has taken place does not necessarily incur stronger sEMG values as opposed to the concave side. An influencing factor to take into consideration could be the degree of the spinal curvature. Nevertheless, the preliminary sEMG examination helps to provide insight on the effectiveness of using a biofeedback system in sEMG postural training. Periodic training with the aid of posture monitoring sensors 140 in a biofeedback system that is custom-made for AIS patients 110 could be very helpful for the patient 110 to maintain a relatively more balanced posture.

C.2. Infrared Thermography [8]

An infrared (IR) thermography was also included for examining the temperature distribution difference between scoliotic and normal subjects. Fourteen normal students (hereinafter referred to as "normal subjects") joined this examination for providing a control result. The normal subjects did not have history of scoliosis nor resulted an ATI>3° from the forward bending test. Table III shows the results of the paired student t-test and Table IV shows the respective temperature distribution. There is no significant difference found for left and right side of the same muscle region in the group of normal subjects. However, the temperature distribution is significantly different at all tested muscle regions in the scoliotic group. The level of statistical significance is p=0.048, 0.000 and 0.012 at the trapezius, latissimus dorsi and quadratus lumborum respectively.

difference at all the tested muscle regions. This can be explained by the observation that the convex side of the observed area has higher IR emission and therefore a higher surface temperature is recorded. The concave side has lower IR emission and thus, a lower surface temperature is recorded. The difference between the convex and concave sides may be a reason for the significant differences found. This above results can also be associated with Zhu et al. [7]. The muscle fiber type I of the scoliotics are significantly less on the concave side of curved spine compared to the convex side, this kind of muscle fiber content asymmetrical leads to the muscle activity imbalance along the paraspinal muscle. As a result, This result demonstrates the possible correlation between spinal deformity and paraspinal muscle activities.

Based on the IR images, an imbalanced temperature distribution was also found between the normal and scoliotic subjects. The IR image of a normal subject has a symmetric temperature distribution along the paraspinal muscles. In contrast, the IR image of a scoliotic subject has an asymmetric pattern along the paraspinal muscles. In the case of a subject (#13) with S-curve of 19.5° at the lumbar region at L3 (right convex) and a minor curve of less than 10° at the thoracic region at T9 (left convex), the IR image recorded a higher temperature at the convex side than the concave side by approximately 0.16° C., 0.27° C. and 0.15° C. (Table V). The results from the IR imaging also demonstrate similarities to the X-ray images of same subject (#13). Therefore, it

TABLE III

Results of paired student t-test for normal and scoliotic group

| Group | N= | Pair | Muscle Region | Mean Difference (° C.) | S.D. | Statistical significance p < 0.05 |
|---|---|---|---|---|---|---|
| Normal | 14 | Pair 1 | Left Trapezius Right Trapezius | −0.053 | 0.148 | |
| | | Pair 2 | Left Latissimus Dorsi Right Latissimus Dorsi | −0.079 | 0.156 | |
| | | Pair 3 | Left Quadratus Lumborum Right Quadrants Lumborum | −0.060 | 0.134 | |
| Scoliosis | 17 | Pair 1 | Left Trapezius Right Trapezius | −0.077 | 0.149 | 0.048 |
| | | Pair 2 | Left Latissimus Dorsi Right Latissimus Dorsi | −0.275 | 0.703 | 0.000 |
| | | Pair 3 | Left Quadratus Lumborum Right Quadrants Lumborum | −0.300 | 0.436 | 0.012 |

TABLE IV

Temperature distribution of normal and scoliotic subjects

| Group | N= | Muscle Region | Mean Temperature (° C.) | S.D. |
|---|---|---|---|---|
| Normal | 14 | Left Trapezius | 32.87 | 0.821 |
| | | Right Trapezius | 32.92 | 0.784 |
| | | Left Latissimus Dorsi | 32.38 | 0.930 |
| | | Right Latissimus Dorsi | 32.46 | 0.941 |
| | | Left Quadratus Lumborum | 31.54 | 0.823 |
| | | Right Quadratus Lumborum | 31.60 | 0.821 |
| Scoliosis | 17 | Left Trapezius | 33.64 | 1.452 |
| | | Right Trapezius | 33.72 | 1.436 |
| | | Left Latissimus Dorsi | 33.00 | 1.46 |
| | | Right Latissimus Dorsi | 33.28 | 1.421 |
| | | Left Quadratus Lumborum | 32.25 | 1.645 |
| | | Right Quadratus Lumborum | 32.55 | 1.645 |

It was found that the paraspinal muscle temperature has no significant difference in all of the tested regions for the normal group, while the scoliotic group shows a significant is believed that IR thermography could reflect an asymmetrical temperature distribution for subjects that have posture defects or symptom of scoliosis.

TABLE V

Temperature distribution of scoliotic subject (#13)

| Cobb's angle | Convex side | Muscle Region | Mean Temp (° C.) | S.D |
|---|---|---|---|---|
| T9 < 10° | Thoracic = Left | Left Trapezius | 33.39 | 0.141 |
| L3 = 19.5° | Thoracolumbar = Right | Right Trapezius | 33.22 | 0.289 |
| | Lumbar = Right | Left Latissimus Dorsi | 33.04 | 0.255 |
| | | Right Latissimus Dorsi | 33.31 | 0.295 |
| | | Left Quadratus Lumborum | 32.52 | 0.191 |
| | | Right Quadratus Lumborum | 32.67 | 0.257 |

C.3. sEMG Posture Training and Result

Twelve subjects recruited from the preliminary examination agreed to participate in the sEMG posture training program. This is a six-month interval after the preliminary examination in accordance with the sEMG posture training as disclosed in section A above. The demographic data of the 12 participants are presented in Table VI. The recommended number of training sessions was about 30 for approximately 6 months. However, only 8 of the 12 subjects had been able to attend at least 30 sessions.

TABLE VI

Demographic data of sEMG posture training participants

| Subject No. | PUMC Curve Type | Convex Side | Height (cm) | Weight (kg) | BMI | Thoracic Angle | Lumbar Angle |
|---|---|---|---|---|---|---|---|
| A | IIc | Right (Thoracic) Left (Lumbar) | 156 | 44.6 | 18.3 | 10.6° | 12.8° |
| B | IIc | Right (Thoracic) Left (Lumbar) | 142 | 39 | 19.3 | 7.9° | 12.1° |
| C | IIc | Right (Thoracic) Left (Lumbar) | 152 | 38.5 | 16.7 | 8.3° | 17.4° |
| D | IIc | Right (Thoracic) Left (Lumbar) | 154 | 49.1 | 20.7 | 10.2° | 17.2° |
| E | Ia | Right (Thoracic) | 163 | 45.1 | 17 | 21.4° | N/A |
| F | Ib | Left (Lumbar) | 154 | 46.3 | 19.5 | N/A | 9.6° |
| G | Ib | Left (Thoracic) | 151 | 53.6 | 23.5 | 17.6° | N/A |
| H | IIc | Right (Thoracic) Left (Lumbar) | 153 | 49.5 | 21.2 | 9.9° | 14.5° |
| I | Ib | Left (Thoracic) Right (Lumbar) | 147 | 35.6 | 16.5 | 3° | 12.3° |
| J | Ia | Right (Thoracic) | 146 | 37.2 | 17.5 | 15.1° | N/A |
| K | Ic | Left (Lumbar) | 156 | 37.1 | 15.2 | N/A | 17.9° |
| L | IIc | Right (Thoracic) Left (Lumbar) | 155 | 40 | 16.5 | 27.6° | 15.4° |

The effectiveness of the sEMG posture training program can be reflected from the training session summary. The customized sEMG posture training with the use of posture monitoring sensors 140 served two purposes for the users. First, it was to encourage the subjects to maintain balance in their muscle activities with less effort by reducing the difference between the sEMG signals on the left and right sides of the tested muscle regions. Second, it was to reduce the sEMG signal value. In order to train the users to achieve the above objectives, visual feedback was provided if the user fulfilled the requirements.

Figure 8:
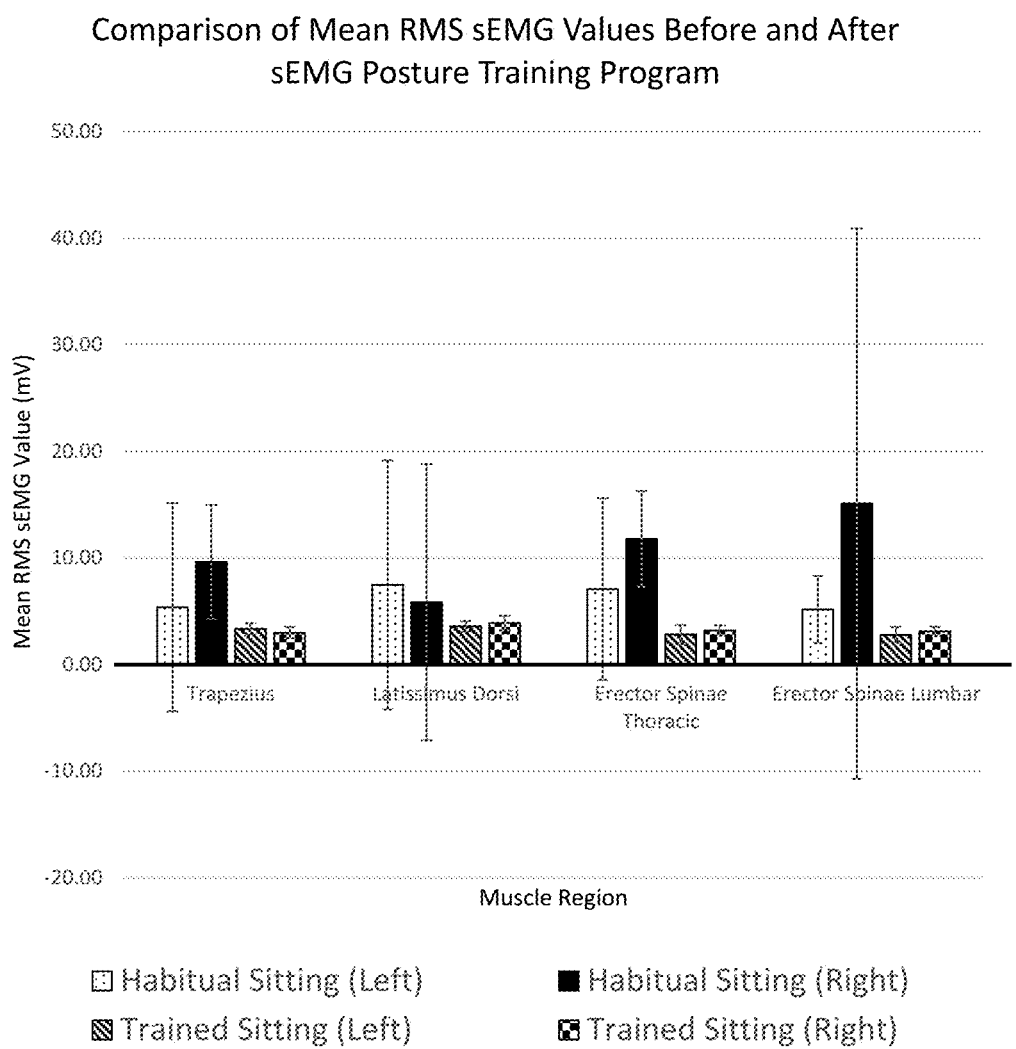
FIG. 8 is a graph summarizing the comparison of mean RMS sEMG values before and after sEMG posture training program.

The sEMG signals processed from each training session of each participant were combined, and a comparison of the data before and after the sEMG posture training was carried out. The result of the posture training is shown in Table VII, as presented by the mean of the RMS sEMG value (mV) before and after the posture training program. For ease of comparison, a bar chart of the results has been generated and shown as FIG. 8.

TABLE VII

Result of mean RMS sEMG values (S.D.) of paraspinal muscles of subjects before and after sEMG posture training program

| | | Mean RMS sEMG value (S.D) (mV) | | | |
| --- | --- | --- | --- | --- | --- |
| N | Muscle Region | Habitual Sitting (Left) | Habitual Sitting (Right) | Trained Sitting (Left) | Trained Sitting (Right) |
| 12 | Trapezius Transversus | 5.365 (9.771) | 9.619 (11.680) | 3.336 (0.524) | 2.974 (0.489) |
| | Latissimus Dorsi | 7.465 (8.521) | 5.840 (3.137) | 3.569 (0.897) | 3.881 (0.730) |
| | Erector Spinae (Thoracic) | 7.066 (5.356) | 11.780 (12.940) | 2.808 (0.527) | 3.176 (0.684) |
| | Erector Spinae (Lumbar) | 5.157 (4.480) | 15.090 (25.810) | 2.776 (0.474) | 3.093 (0.432) |

Two observations can be made based on the above results from the sEMG posture training. The first observation is that the subjects have a relatively lower sEMG activity in their sitting posture after the training. Before the training, none of the mean RMS sEMG values are less than 5 mV among all of the tested muscle regions. The highest value is on the right side of the erector spinae at the lumbar region which recorded an average of 15.09 mV. This indicates that the subjects have higher muscle activities in the sitting posture. After around 30 sessions of sEMG posture training, the mean RMS sEMG value significantly dropped to less than 4 mV. The highest value is the right side of the latissimus dorsi which recorded 3.881 mV. This result satisfies one of the objectives of the sEMG posture training for performing the same motion of sitting with less muscle activities. As it is obvious that fatigue is caused by constant static muscular work, it is recommended that the level of muscle activities should be minimized at all possible levels when sitting. The result positively indicates the effectiveness of the biofeedback training system by assisting the patient to relax the muscle regions through self-regulation.

The second observation is that the standard deviation is lower after the training. This means that the data distribution across the 12 subjects is comparatively more evenly distributed than before the training. The training successfully trained the subjects to maintain a certain level of muscle activities throughout the training sessions.

Figure 9:
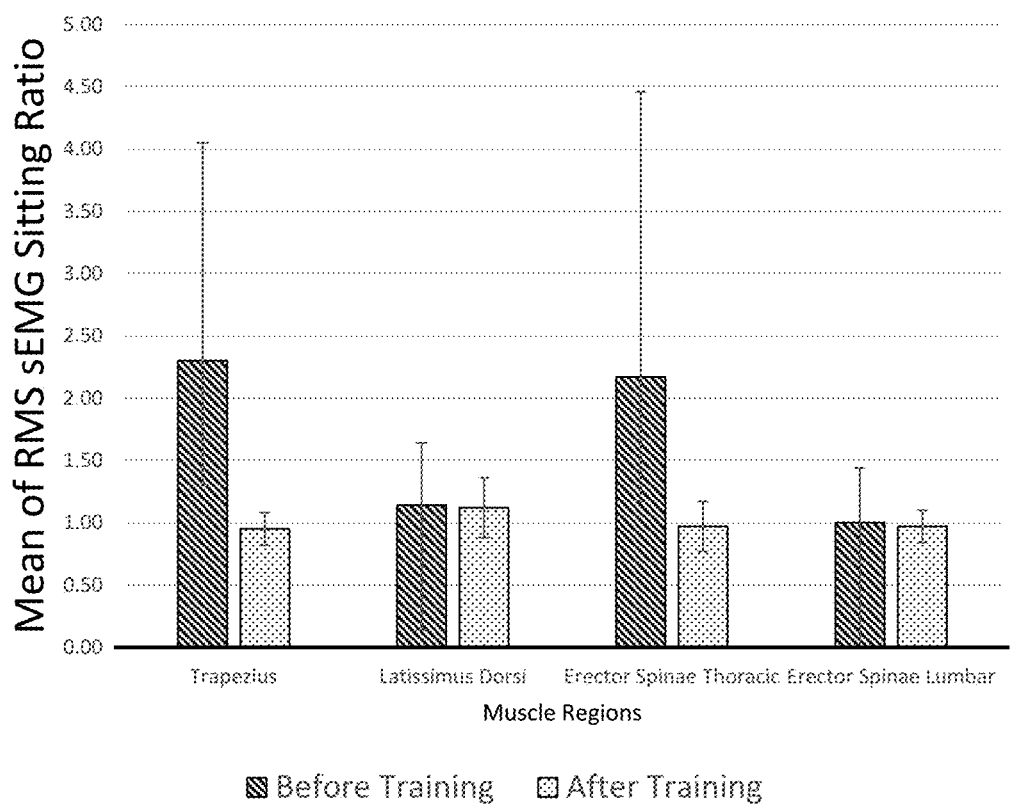
FIG. 9 is a graph summarizing the comparison of mean RMS sEMG ratio before and after sEMG posture training program.

It should be noted that the mean RMS sEMG value is not meant to be used for direct comparison among the different subjects as the data were not normalized, and the maximum voluntary contraction of each muscle region of each subject may differ. Therefore, the sEMG value is calculated as a sEMG ratio to normalize the data for analysis, and summarized in FIG. 9 and Table VIII.

TABLE VIII

Result of mean RMS sEMG ratio (S.D.) of paraspinal muscles of subjects before and after sEMG posture training program

| | | Mean RMS sEMG ratio (S.D) | |
| --- | --- | --- | --- |
| N | Muscle Region | Before Training | After Training |
| 8 | Trapezius Transversus | 2.30 (1.75) | 0.95 (0.13) |
| | Latissimus Dorsi | 1.14 (0.50) | 1.12 (0.24) |
| | Erector Spinae (Thoracic) | 2.17 (2.29) | 0.97 (0.20) |
| | Erector Spinae (Lumbar) | 1.00 (0.44) | 0.97 (0.13) |

Another important purpose of the sEMG posture training is to train the patients to sit with a more balanced posture as quantified by a sEMG signal. The mean RMS sEMG ratio is a good index for indicating the level of symmetrical muscle activities during the sitting posture. The users should ideally obtain a ratio of 1 in which the left and right sides of the same muscle region have perfectly symmetrical muscle activities. From the data obtained before and after the training program, the mean ratios at all tested muscle regions except erector spinae at lumbar regions had an improvement in terms of sEMG sitting ratio after 30 sessions of training. Therefore, the subjects have a significant improvement on the balance of their posture after the training.

C.4. Evaluation of Posture Before and after Training

Figure 10:
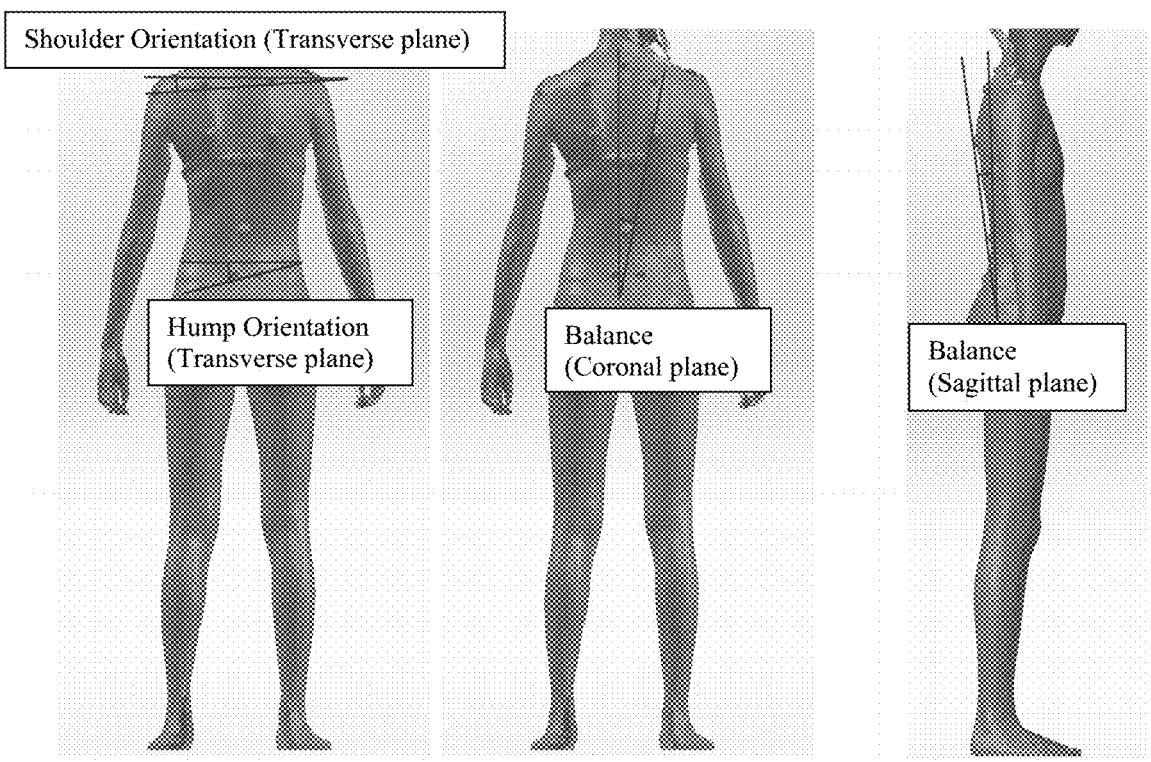
FIG. 10 is a representation of the measurement of posture indices in 3D body scanning with anatomic landmarks.

Before and after the sEMG posture training, 3D body scanning was arranged for eleven of the subjects (FIG. 10). From the result of the posture evaluation, it is observed that there is a general improvement in their posture in terms of the mean angles except for balance (Coronal plane). The results are summarized as follow in Table IX.

TABLE IX

Measured mean angles of subjects before and after sEMG posture training

| | | Mean Angle (°) (S.D.) | |
| --- | --- | --- | --- |
| Measured Item | N | Before | After |
| Shoulder Orientation (Transverse plane) | 11 | 1.56 (0.95) | 1.09 (0.83) |
| Hump Orientation (Transverse plane) | | 2.84 (2.44) | 2.72 (1.85) |
| Balance (Coronal plane) | | 1.97 (1.53) | 2.13 (1.68) |
| Balance (Sagittal plane) | | 1.43 (0.95) | 1.12 (0.64) |

The effectiveness of the sEMG training in controlling the spinal deformity of AIS patients was further assessed by comparing the spinal curvature of each subject using Scolioscan™ before the training started and 6 months after the training was completed [6]. The results are summarized as follow in Table X.

TABLE X

Changes in spinal curvature before and after the posture training

| Subject No. | 0 Month | | 6 Month | | Difference | |
|---|---|---|---|---|---|---|
| | Thoracic Angle (°) | Lumbar Angle (°) | Thoracic Angle (°) | Lumbar Angle (°) | Thoracic Angle (°) | Lumbar Angle (°) |
| A | 10.6 | 12.8 | 12 | 14.5 | 1.4 | 1.7 |
| B | 7.9 | 12.1 | 8.2 | 9.8 | 0.3 | −2.3 |
| C | 8.3 | 17.4 | 10.2 | 15.1 | 1.9 | −2.3 |
| D | 10.2 | 17.2 | 9.6 | 15.8 | −0.6 | −1.4 |
| E | 21.4 | N/A | 25.3 | N/A | 3.9 | N/A |
| F | N/A | 9.6 | N/A | 10.3 | N/A | 0.7 |
| G | 17.6 | N/A | 11.9 | N/A | −5.7 | N/A |
| H | 9.9 | 14.5 | 16.1 | 21.3 | 6.2 | 6.8 |
| I | 3 | 12.3 | 7.9 | 10.9 | 4.9 | −1.4 |
| J | 15.1 | N/A | 16.5 | N/A | 1.4 | N/A |
| K | N/A | 17.9 | N/A | 16.2 | N/A | −1.7 |
| L | 27.6 | 15.4 | 22 | 15.4 | −5.6 | 0 |

Based on the definition of the effectiveness of scoliosis treatment, an increase of more than 5° in the Cobb's angle is considered as curve progression, an increase of 5° or less in the Cobb's angle is defined as no progression, while a decrease or no change in the Cobb's angle is defined as a reduction in the Cobb's angle. Both "no progression" and "reduction" are considered as an improvement of the spinal curve. [5]

Figure 11:
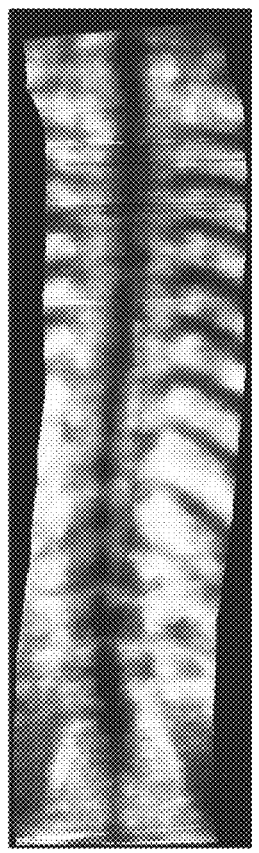
FIG. 11 is the Scolioscan™ images before and after the sEMG posture trainings for subject G.
Figure 11:
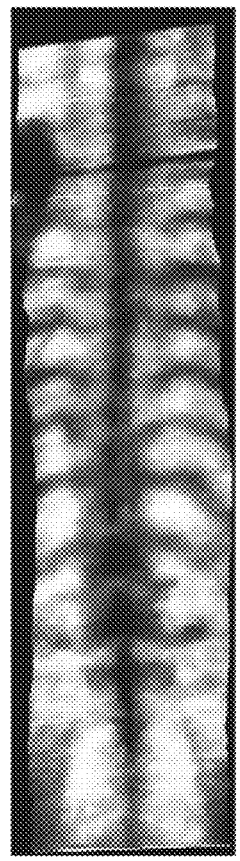
Figure 12:
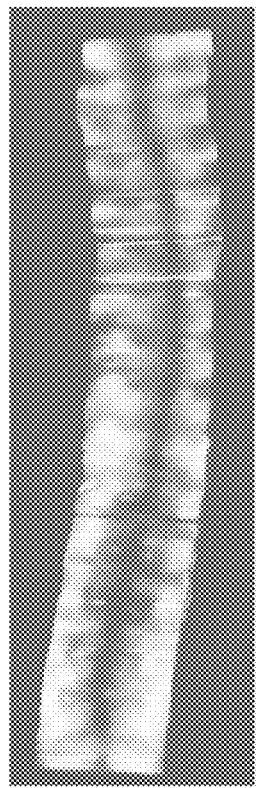
FIG. 12 is the Scolioscan™ images before and after the sEMG posture trainings for subject L.
Figure 12:
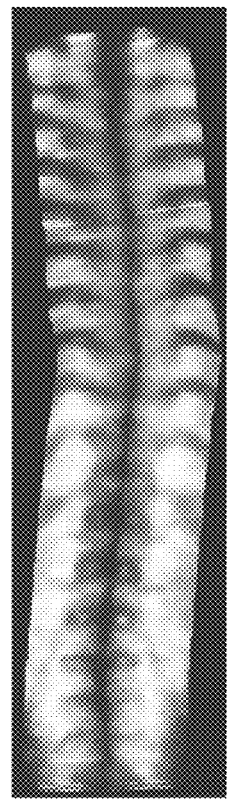

Among the 12 subjects, one subject (H) had a progression for more than 5°, nine subjects had no progression and two subjects (G and L) had improvement of spinal curve. Particularly, it is clear that subject G had a spinal curvature reduction of 5.7° and subject L had a spinal curvature reduction of 5.6°, but resulting in a relatively straighter spine. The Scolioscan™ images before and after the sEMG posture trainings are compared in FIG. 11 and FIG. 12. Subject H progressed 6.2° and 6.8° for both the thoracic and lumbar regions compared to her spinal situation before training. The reason for the progression may be due to her lack of attendance. She had only attended 25 sessions of the sEMG posture trainings, which is the lowest attendance among all of the subjects. The other subjects were able to demonstrate an improvement in their spinal deformity or progressed within control. In this trial test, the control rate is 91.67%.

Figure 13:
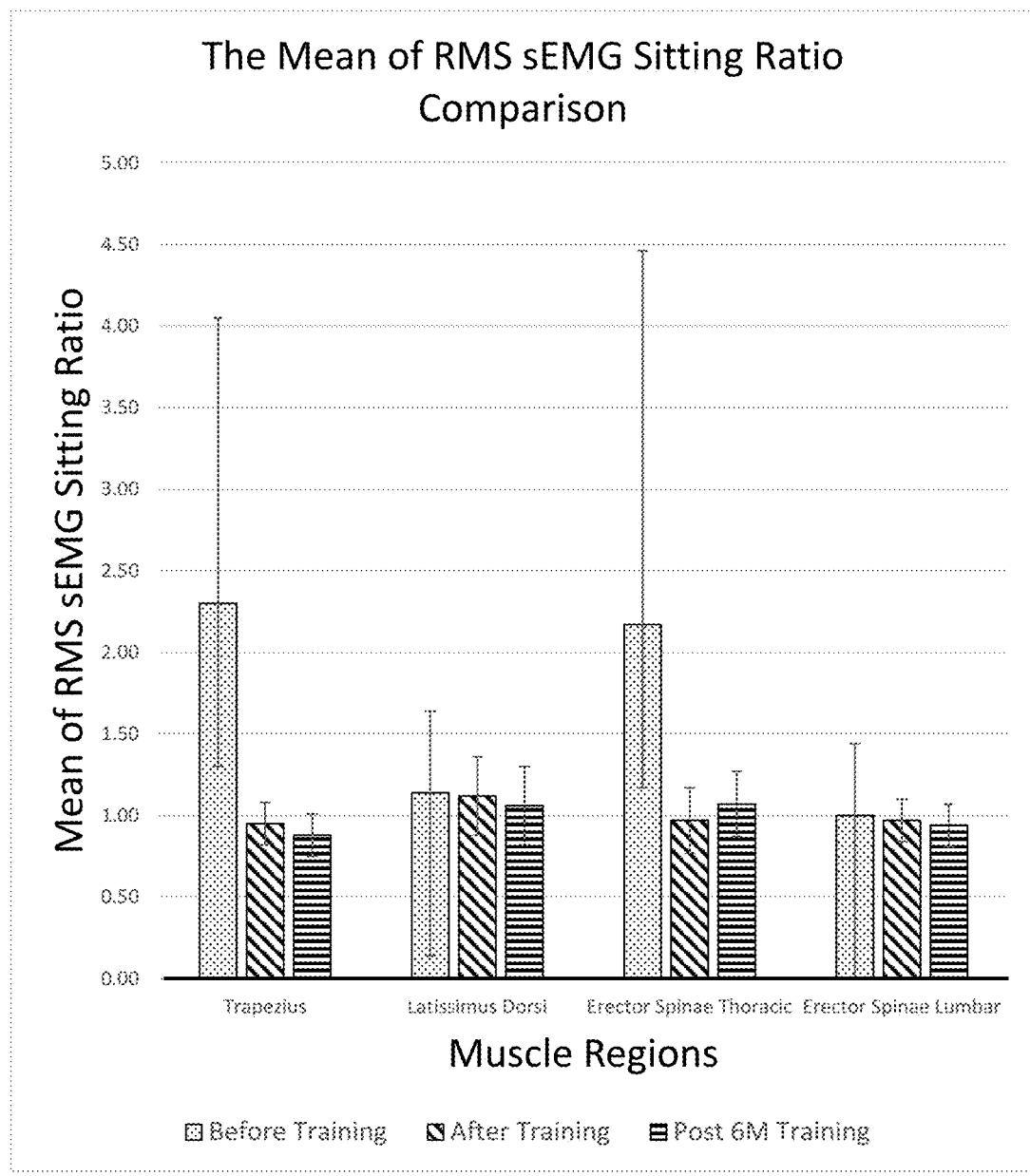
FIG. 13 is a graph summarizing the comparison of mean RMS sEMG ratio for 6 months post-training as compared with the ratio before and after sEMG posture training program.

A follow-up inspection for the subjects was provided after another six months from the sEMG posture trainings. The inspection included a sEMG examination and Scolioscan™. This inspection was aimed to inspect the carry-over effect of the sEMG posture training after an extra six months. The results are shown in FIG. 13.

The result showed that the RMS sEMG ratios are not as balanced as the record after 30 sessions of training. However, the status of the muscle balance in terms of sEMG signal did not change back to the imbalanced situation as before the training. The currently disclosed method of biofeedback training is therefore able to train the participants to maintain a better posture. The motor learning process also helped them memorized the posture.

CITED REFERENCES

The following documents are cited in this patent application. References [1]-[7] are incorporated by reference herein.

[1] McKenzie R., "Treat Your Own Back", Spinal Publications New Zealand Ltd., 1980.
[2] Dolan L. A. et al., "Professional opinion concerning the effectiveness of bracing relative to observation in adolescent idiopathic scoliosis", Journal of Pediatric Orthopaedics, 27(3): 270276, 2007.
[3] Wong M. S., et al., "The Effect of Rigid Versus Flexible Spinal Orthosis on the Clinical Efficacy and Acceptance of the Patients With Adolescent Idiopathic Scoliosis", SPINE, 33 (12), 1360-1365, 2008.
[4] Dworkin, B., et al., "Behavioral Method for the Treatment of Idiopathic Scoliosis", Medical Sciences, 82 (8), 2493-2497, 1985.
[5] Wong W., "Development of a posture monitoring system", Department of Health Technology and Informatics, The Hong Kong Polytechnic University, 2009.
[6] Zheng Y. P., "3D Ultrasound Imaging for Assessment of Scoliosis", The Spine Journal, 12 (9), S164, 2012.
[7] Zhu, Z., et al., "Genome-wide association study identifies novel susceptible loci and highlights Wnt/beta-catenin pathway in the development of adolescent idiopathic scoliosis", Human molecular genetics, 26, (8), 1577-1583, 2017.
[8] Kwok, G., et al., "Postural Screening for Adolescent Idiopathic Scoliosis with Infrared Thermography", Scientific Report, Nature, 7:14431, 31 Oct. 2017.

What is claimed is:

1. A biofeedback system for monitoring patient-related signals of a patient having adolescent idiopathic scoliosis (AIS), providing a personalized biofeedback to the patient based on the patient-related signals, and providing posture trainings to the patient by restoring a balance in muscle activities and reducing a displacement of both sides of the patient's spine as a treatment for AIS, the system comprising:
   a garment integrated with one or more posture monitoring sensors, wherein each posture monitoring sensor comprises a 3-axis accelerometer; and
   one or more computational systems comprising a sensor-based surface electromyographic (sEMG) posture training subsystem and a posture monitoring subsystem wherein:
      the sensor-based sEMG posture training subsystem comprises:
         a posture training device, coupled to a plurality of sEMG sensors, for triggering a feedback device as a motivation program facilitating the patient to balance the muscle activities, and determining a calibration function for synchronizing the sEMG sensors with the posture monitoring sensors as a calibration for the posture monitoring sensors, wherein the calibration function determines ranges of preferred patient-related signals when the posture training device determines that both sides of the patient's spine are balanced.

2. The biofeedback system of claim 1, wherein the posture monitoring subsystem comprises a mobile processor configured to be communicable with the posture monitoring sensors on the garment for aggregating the patient-related signals of the patient through daily activities and determining a properness of the posture; and to provide a real-time feedback to the patient on the properness of the posture.

3. The biofeedback system of claim 2, wherein the mobile processor is used for analyzing the patient's posture by comparing the aggregated patient-related signals through daily activities with the ranges of preferred patient-related signals.

4. The biofeedback system of claim 2, wherein the determining of the properness of the posture is implemented on a cloud infrastructure.

5. The biofeedback system of claim 2, wherein the posture monitoring system further comprises a database for storing the real-time data of the patient's posture through daily activities.

6. The biofeedback system of claim 5, wherein the database is accessible by doctors or specialists for a long-term real-time surveillance on a progress of the patient.

7. The biofeedback system of claim 2, wherein the mobile processor is a processor of a mobile device such as a smart-phone, a smart-watch, or a tablet, and controls a mobile application for providing the real-time feedback to the patient on the properness of the posture.

8. The biofeedback system of claim 7, wherein the mobile application is designed to provide a visual summary with respect to the information obtained from the posture monitoring sensors for the patient to monitor.

9. The biofeedback system of claim 7, wherein the mobile application is developed on one or more operation systems including iOS or Android.

10. The biofeedback system of claim 1, wherein the plurality of sEMG sensors further comprises a first sEMG sensor and a second sEMG sensor placed on a pair of paraspinal muscles of the patient for evaluating a myoelectric activity of the pair of paraspinal muscles quantitatively based on a concave sEMG signal and a convex sEMG signal respectively.

11. The biofeedback system of claim 10, wherein the concave sEMG signal and the convex sEMG signal are used to determine a root-mean-square (RMS) sEMG ratio for indicating a symmetric level of the pair of paraspinal muscles based on:

$$\text{RMS } sEMG \text{ Ratio} = \frac{\text{RMS } sEMG(\text{convex})}{\text{RMS } sEMG(\text{concave})}$$

12. The biofeedback system of claim 11, wherein the RMS sEMG ratio is used to determine the visual feedback to the patient, and the patient adjusts the balance in muscle activities based on the visual feedback such that the RMS sEMG ratio can be as close to 1 as possible.

13. The biofeedback system of claim 10, wherein the concave sEMG signal and the convex sEMG signal are filtered by one or more band pass filters and a notch filter.

14. The biofeedback system of claim 1, wherein the one or more posture monitoring sensors are positioned at locations proximate to T3, T12 and L4-L5 of the patient's spine.

15. The biofeedback system of claim 1, wherein each of the posture monitoring sensors further comprises a microcontroller unit (MCU) with a wireless communication interface.

16. The biofeedback system of claim 1, wherein the one or more posture monitoring sensors further comprise one or more additional sensors selected from a gyroscope, and a temperature sensor.

17. The biofeedback system of claim 1, wherein the garment is fabricated as a body-mapping tank-top for accommodating the posture monitoring sensors on a posterior and medial part of the torso of body-mapping tank-top along the patient's spine.

18. The biofeedback system of claim 1, wherein the wireless communication interface is configured to support one or more communication protocols for communicating with the posture training device and the portable electronic device, the one or more protocols being selected from Bluetooth, Wireless Body Area Network (WBAN), including inter-integrated circuit ($I^2C$), and serial (COM) communication.

19. The biofeedback system of claim 1, wherein the feedback device is a visual screen used for displaying an animation as the motivation program facilitating the patient to balance the muscle activities.

* * * * *